United States Patent
Oh et al.

(10) Patent No.: US 9,603,577 B2
(45) Date of Patent: Mar. 28, 2017

(54) X-RAY IMAGING APPARATUS AND CONTROL METHOD THEREOF

(71) Applicant: SAMSUNG ELECTRONICS CO., LTD., Suwon-si (KR)

(72) Inventors: Hyun Hwa Oh, Hwaseong-si (KR); Dong Goo Kang, Hwaseong-si (KR); Sung Hoon Kang, Suwon-si (KR); Young Hun Sung, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 282 days.

(21) Appl. No.: 14/303,905

(22) Filed: Jun. 13, 2014

(65) Prior Publication Data

US 2014/0369472 A1 Dec. 18, 2014

(30) Foreign Application Priority Data

Jun. 13, 2013 (KR) ........................ 10-2013-0068034

(51) Int. Cl.
*A61B 6/00* (2006.01)
*A61B 6/06* (2006.01)

(52) U.S. Cl.
CPC ................ *A61B 6/484* (2013.01); *A61B 6/06* (2013.01); *A61B 6/4266* (2013.01); *A61B 6/4417* (2013.01); *A61B 6/463* (2013.01)

(58) Field of Classification Search
CPC ......... A61B 6/484; A61B 6/06; A61B 6/4266; A61B 6/4417; A61B 6/463
See application file for complete search history.

(56) References Cited

U.S. PATENT DOCUMENTS

| 4,763,343 A * | 8/1988 | Yanaki ................... A61B 6/502 378/110 |
| 6,408,049 B1 | 6/2002 | Edic et al. |
| 2003/0081734 A1 * | 5/2003 | Nicolas ............... A61B 6/0457 378/205 |
| 2004/0131145 A1 * | 7/2004 | Ohara ................... A61B 6/484 378/37 |

(Continued)

FOREIGN PATENT DOCUMENTS

| JP | 2003-151795 A | 5/2003 |
| JP | 2005-6782 A | 1/2005 |

(Continued)

*Primary Examiner* — Glen Kao
(74) *Attorney, Agent, or Firm* — Sughrue Mion, PLLC

(57) ABSTRACT

An X-ray imaging apparatus and control method for the X-ray imaging apparatus are provided. The X-ray imaging apparatus includes an X-ray source to generate X-ray beams, and to irradiate the X-ray beams onto an object; a first X-ray detector configured to detect X-ray beams transmitted through the object and generate a first phase contrast signal; an X-ray obtainer including an X-ray collimator and a second X-ray detector, wherein the X-ray collimator is spaced apart from the object by a predetermined distance, and configured to focus the X-ray beams transmitted through the object, and wherein the second X-ray detector is configured to detect the focused X-ray beams and generate a second phase contrast signal based on the detected X-ray beams; and an image processor configured to create a phase contrast image and an absorption image of the object.

23 Claims, 25 Drawing Sheets

(56) References Cited

U.S. PATENT DOCUMENTS

| | | | |
|---|---|---|---|
| 2006/0039532 A1* | 2/2006 | Wu | A61B 6/484 378/62 |
| 2010/0067648 A1* | 3/2010 | Kojima | A61B 6/0414 378/11 |
| 2013/0129051 A1* | 5/2013 | Nakano | G01N 23/20 378/71 |
| 2014/0079184 A1* | 3/2014 | Das | A61B 6/484 378/62 |

FOREIGN PATENT DOCUMENTS

| | | | | |
|---|---|---|---|---|
| KR | 10-1239765 B1 | 3/2013 | | |
| WO | WO 2012014982 A1 * | 2/2012 | | G01N 23/207 |

* cited by examiner

MOVEMENT OF X-RAY DETECTOR

X-RAY IMAGING APPARATUS AND CONTROL METHOD THEREOF

CROSS-REFERENCE TO RELATED APPLICATION

This application claims priority from Korean Patent Application No. 10-2013-0068034, filed on Jun. 13, 2013 in the Korean Intellectual Property Office, the disclosure of which is incorporated herein by reference in its entirety.

BACKGROUND

1. Field

Methods and apparatuses consistent with exemplary embodiments relate to an X-ray imaging apparatus for generating an X-ray image by transmitting X-ray beams through an object, and a control method thereof.

2. Description of the Related Art

An X-ray imaging apparatus is an imaging apparatus for visualizing the inside of an object, such as a body part of a human, by irradiating X-ray beams onto the object and detecting X-ray beams transmitted through the object.

Conventional X-ray imaging apparatuses visualize the inside structure of an object according to the intensities of X-ray beams transmitted through the object, based on a fact that X-ray beams show different attenuation or absorption characteristics depending on the properties of materials constituting the object.

In view of electromagnetic waves, when X-ray beams are transmitted through an object, the X-ray beams are refracted by and interfered with the materials making up the object so that the phases of the X-ray beams are shifted. Phase shift characteristics of X-ray beams depend on the properties of materials. Recently, phase contrast imaging technology in which the inside of an object is visualized using the phase contrast of X-ray beams is being developed.

Since X-ray beams have a great phase shift coefficient rather than an absorption coefficient with respect to materials, the phase contrast imaging technology can acquire an image of high contrast with a low dose of X-rays and also can reduce a dose of radiation. Accordingly, more studies into such phase contrast imaging technology are needed.

SUMMARY

Therefore, an aspect of an exemplary embodiment provides an X-ray imaging apparatus capable of acquiring an image signal corresponding to a Full Field Of View (Full FOV) image of an object with an X-ray detector having a small size for detecting an X-ray signal transmitted through the object, by placing an X-ray collimator in front of the X-ray detector to focus X-ray beams on a predetermined area, and a control method of the X-ray imaging apparatus.

Additional aspects of the exemplary embodiments will be set forth in part in the description which follows and, in part, will be obvious from the description, or may be learned by practice of the exemplary embodiments.

In accordance with an aspect of an exemplary embodiment, an X-ray imaging apparatus includes, an X-ray source configured to generate X-ray beams, and to irradiate the X-ray beams onto an object, a first X-ray detector located adjacent to the object, and configured to detect X-ray beams transmitted through the object and generate a first phase contrast signal based on the detected X-ray beams, an X-ray obtainer including an X-ray collimator and a second X-ray detector, wherein the X-ray collimator is spaced apart from the object by a predetermined distance, and configured to focus the X-ray beams transmitted through the object, and wherein the second X-ray detector is configured to detect the focused X-ray beams and generate a second phase contrast signal based on the detected X-ray beams, and an image processor configured to create a phase contrast image and an absorption image about the object based on the first phase contrast signals generated by the first X-ray detector and the second phase contrast signal generated by the second X-ray detector.

The X-ray collimator may use polycapillary optics.

The second X-ray detector may detect the X-ray beams focused by the X-ray collimator and generate a phase contrast signal based on the detected X-ray beams.

The second X-ray detector may detect the X-ray beams focused by the X-ray collimator after the first X-ray detector is removed or bent at a predetermined angle.

The X-ray source may generate a spatial coherent X-ray beam.

Each of the first X-ray detector and the second X-ray detector may be a Photon Counting Detector (PCD) configured to count a number of photons having higher energy value than a threshold energy value corresponding to each of a plurality of energy bands among photons included in the detected X-ray, and wherein each of the first X-ray detector and the second X-ray detector may divide the detected X-ray beams according to the plurality of energy bands, and generate a phase contrast image signal for each of the plurality of energy bands.

The X-ray imaging apparatus may further include an exposure controller configured to set one or more conditions that are applied during radiography by analyzing a pre-shot image of the object.

The exposure controller may analyze the pre-shot image to determine properties of the object, and adjust a focal spot size of the X-ray source based on the properties of the object.

The exposure controller may adjust at least one of a distance between the X-ray source and the object and a distance between the object and the X-ray obtainer, based on at least one of the properties of the object, a focal spot size of the X-ray source, and a Field Of View (FOV) of the X-ray source.

The X-ray imaging apparatus may further include a display configured to display the phase contrast image and the absorption image of the object.

In accordance with another aspect of an exemplary embodiment, a control method of an X-ray image apparatus includes generating first X-ray beams, and irradiating the first X-ray beams onto an object, detecting by a first X-ray detector first X-ray beams transmitted through the object, dividing the detected first X-ray beams according to a first plurality of energy bands, and generating a first phase contrast image signal for each of the first plurality of energy bands, generating second X-ray beams, and irradiating the second X-ray beams onto the object, focusing X-ray beams transmitted through the object at an X-ray collimator which is spaced apart from the object by a predetermined distance, detecting by a second X-ray detector coupled with the X-ray collimator the focused X-ray beams, dividing the detected second X-ray beams according to a second plurality of energy bands, and generating a second phase contrast image signal for each of the second plurality of energy bands, and creating a phase contrast image and an absorption image of the object based on the first phase contrast image signal generated for each of the first plurality of energy bands and the second phase contrast image signal generated for each of the second plurality of energy bands.

The first X-ray beams and the second X-ray beams are spatial coherent X-ray beams.

The generating the second phase contrast image signal for each of the second plurality of energy bands may be performed after the first X-ray detector located adjacent to the object is removed or bent at a predetermined angle.

The generating the first phase contrast image signal for each of the first plurality of energy bands and the generating the second phase contrast image signal for each of the second plurality of energy bands may include counting a number of photons having a higher energy value than a threshold energy value corresponding to each of the first plurality of energy bands and the second plurality of energy bands among photons included in the detected first X-ray beams and the second X-ray beams, respectively.

The control method may further include: carrying out pre-shot imaging of the object to acquire a pre-shot image of the object, and analyzing the pre-shot image of the object to set one or more conditions that are applied during radiography.

The control method may further include displaying the phase contrast image and the absorption image of the object.

In accordance with another aspect of an exemplary embodiment, a control method of an X-ray imaging apparatus includes generating first X-ray beams, and irradiating the first X-ray beams onto an object, at an X-ray detector located adjacent to the object, detecting the first X-ray beams transmitted through the object, and generating a first phase contrast signal based on the detected first X-ray beams, generating the second X-ray beams, and irradiating the second X-ray beams onto the object, at an X-ray collimator which is spaced apart from the object by a predetermined distance, focusing the second X-ray beams transmitted through the object, at a second X-ray detector coupled with the X-ray collimator, detecting the focused second X-ray beams, and generating a second phase contrast signal based on the detected second X-ray beams, and creating a phase contrast image and an absorption image of the object based on the first phase contrast signal and the second phase contrast signal.

The first X-ray beams and the second X-ray beams may be spatial coherent X-ray beam.

The generating the second phase contrast signal for each of the second plurality of energy bands is performed after the first X-ray detector located adjacent to the object is removed or bent at a predetermined angle.

The control method may further include displaying the phase contrast image and the absorption image of the object.

Therefore, according to the X-ray imaging apparatus and the control method thereof as described above, it is possible to acquire an image signal corresponding to a Full Field of View (Full FOV) image of an object with an X-ray detector having a small size for detecting an X-ray signal transmitted through the object, by disposing an X-ray collimator in front of the X-ray detector to focus X-ray beams on a predetermined area.

BRIEF DESCRIPTION OF THE DRAWINGS

These and/or other aspects will become apparent and more readily appreciated from the following description of the exemplary embodiments, carried out in conjunction with the accompanying drawings of which.

DETAILED DESCRIPTION

Figure 1:
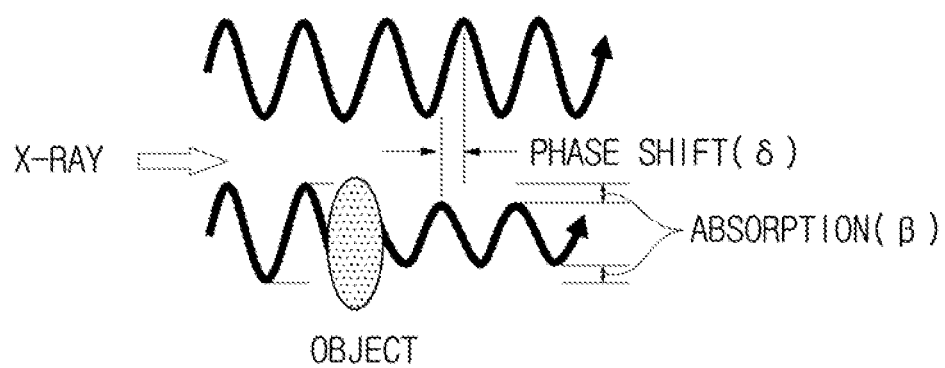
FIG. 1 is a view for describing a phenomenon that occurs when an X-ray beam is transmitted through an object.

Reference will now be made in detail to the exemplary embodiments, examples of which are illustrated in the accompanying drawings, wherein like reference numerals refer to like elements throughout.

FIG. 1 is a view for describing a phenomenon that occurs when an X-ray beam is transmitted through an object, such as a body part of a human. However, the exemplary embodiments are not limited to imaging parts of a human and other types of objects can be imaged.

X-ray beams having both a particle nature and a wave nature can be considered as electromagnetic waves. When an X-ray beam is transmitted through an object, the amplitude of the X-ray beam is reduced and phase shift ($\delta$) is generated, as illustrated in FIG. 1. The amplitude of the X-ray beam is reduced because a part of the X-ray beam is absorbed by a material constituting the object, which is called X-ray attenuation.

Figure 2:
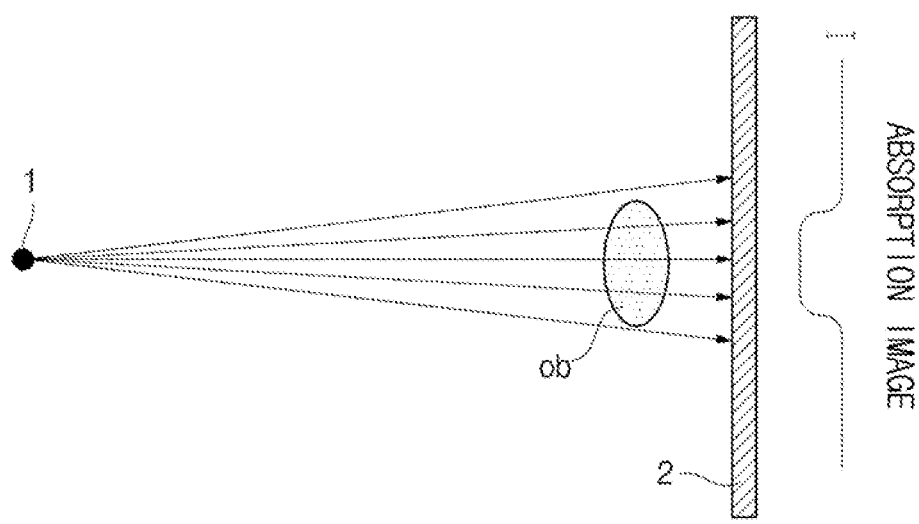
FIG. 2 is a view for describing a process of acquiring an X-ray image using the attenuation characteristics of X-ray beams.

FIG. 2 is a view for describing a process of acquiring an X-ray image using the attenuation characteristics of X-ray beams.

X-ray beams show different attenuation characteristics depending on the different materials constituting an object. In other words, different materials constituting an object absorb X-ray beams at different absorption rates. In this specification, an image created based on the attenuation characteristics of X-rays will be referred to as an absorption image. In order to create an absorption image of a certain object ob, as illustrated in FIG. 2, an X-ray source 1 generates X-ray beams, and irradiates the X-ray beams onto an object ob, and an X-ray detector 2 detects X-ray beams transmitted through the object ob. Since the intensities of the detected X-ray beams include information regarding X-ray attenuation, an absorption image of the object ob can be created using the intensities of the detected X-ray beams.

Figure 3:
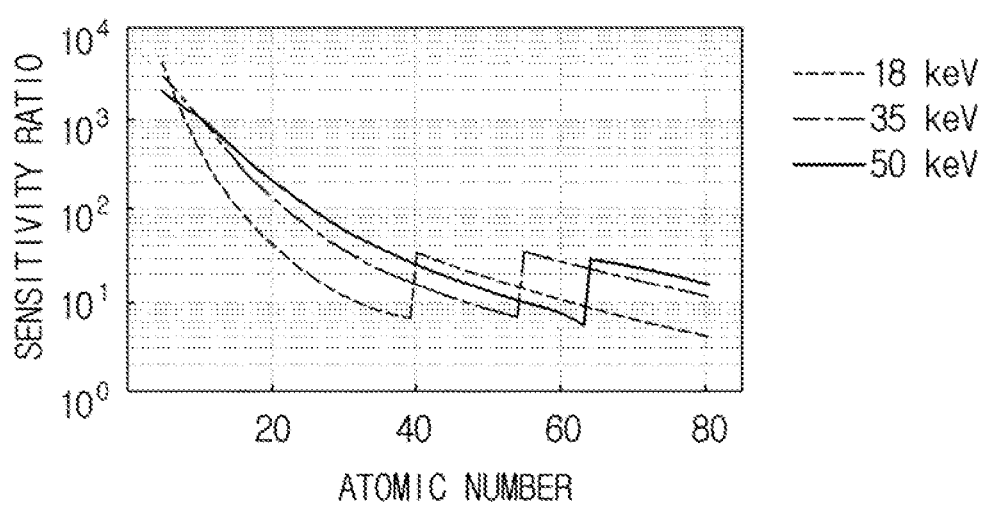
FIG. 3 is a graph showing sensitivity ratios of the phase shift characteristics of X-ray beams with respect to the attenuation characteristics of X-ray beams.

FIG. 3 is a graph showing the sensitivity ratios of the phase shift characteristics of X-ray beams with respect to the attenuation characteristics of the X-ray beams.

The phases of X-ray beams change when they are transmitted through an object because X-ray beams are refracted by and interfered with a material constituting the object. If an index representing the attenuation characteristics of X-ray beams is denoted by $\beta$, and an index representing the phase shift characteristics of X-ray beams is denoted by $\delta$, a ratio $\delta/\beta$ of the phase shift characteristics $\delta$ of X-rays with respect to the attenuation characteristics $\beta$ of X-rays is a sensitivity ratio, which is illustrated in FIG. 3. As shown in FIG. 3, the phase shift characteristics $\delta$ of X-ray beams are up to several thousands of times more sensitive than the attenuation characteristics $\delta$ of X-ray beams although the sensitivity ratio $\delta/\beta$ depends on the energy of the X-ray beams and materials constituting an object.

Figure 4A:
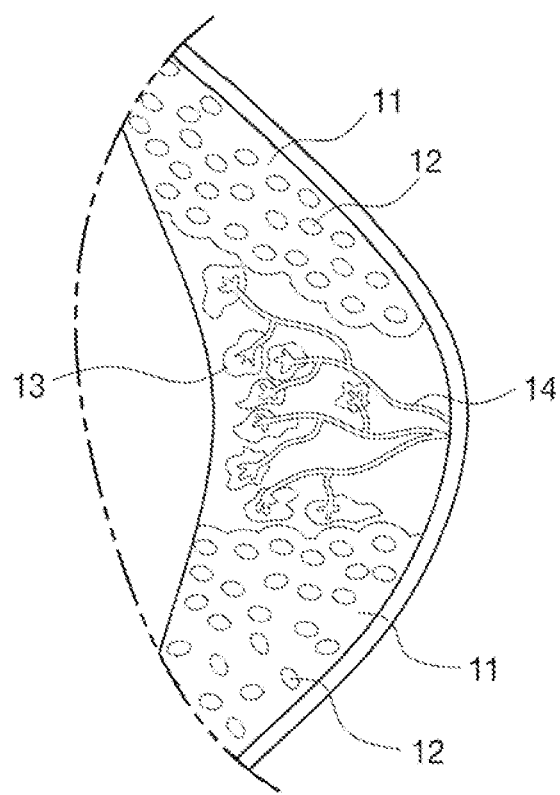
FIG. 4A illustrates the inner materials of a breast.
Figure 4B:
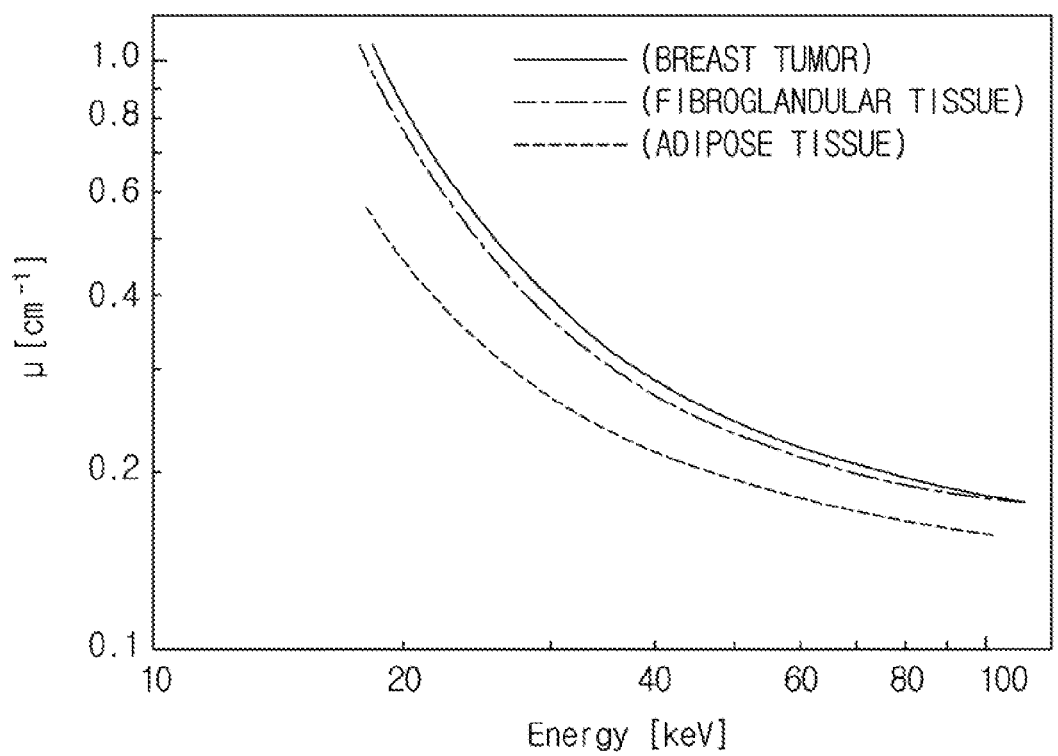
FIG. 4B is a graph showing attenuation coefficients of the inner materials of the breast.

FIG. 4A illustrates the inner materials of a breast, and FIG. 4B is a graph showing attenuation coefficients of the inner materials of the breast.

Referring to FIG. 4A, the inner tissue of a breast 10 is comprised of fibrous tissue 11 surrounding the breast 10 and maintaining the shape of the breast 10, adipose tissue 12 distributed over the whole area of the breast 10, mammary tissue 13 to make breast milk, and duct tissue 14 which are transfer ducts for breast milk, etc. Tissue, such as the mammary tissue 13 and the duct tissue 14, are involved in making and supplying breast milk among the above-mentioned tissue is called fibroglandular tissue. Fibroglandular tissue has an attenuation coefficient $\mu$ similar to that of lesions such as a tumor, as illustrated in FIG. 4B.

Furthermore, since the breast 10 consists of only soft tissue, the inner materials of the breast 10 have little differences in X-ray attenuation characteristics, as seen from FIG. 4B. Accordingly, it is difficult to acquire accurate information about the inner materials of a breast when only an absorption image is used.

As illustrated in FIG. 3, since the phase shift characteristics of X-ray beams are several tens to thousands of times more sensitive than the attenuation characteristics of X-ray beams, in the case of an object such as a breast, whose inner materials have little differences in X-ray attenuation characteristics, the phase shift characteristics of X-ray beams can be used to obtain a clearer X-ray image.

Technology for visualizing the inside of an object based on the fact that different materials constituting an object have different phase shift characteristics of X-ray beams is called phase contrast imaging technology. An image created by the phase contrast imaging technology is called a phase contrast image.

Methods for creating a phase contrast image include interferometry, grating interferometry, diffraction-enhanced imaging, and in-line phase contrast imaging. The in-line phase contrast imaging does not require a separate optical element such as a diffractive grating or a reflector, and can be embodied with elements similar to those of a general X-ray imaging apparatus. Accordingly, it is assumed that an X-ray imaging apparatus according to an exemplary embodiment acquires phase contrast images using the in-line phase contrast imaging.

Figure 5A:
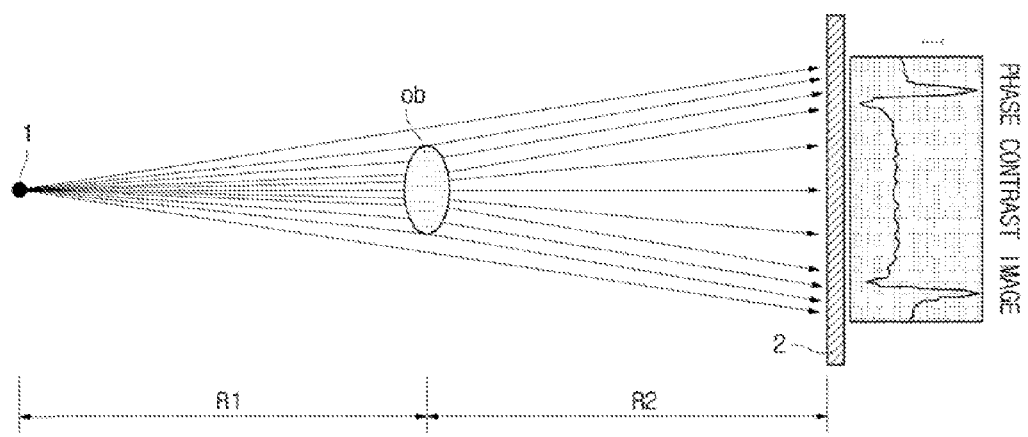
FIG. 5A is a view for describing a process of acquiring a phase contrast image.
Figure 5B:
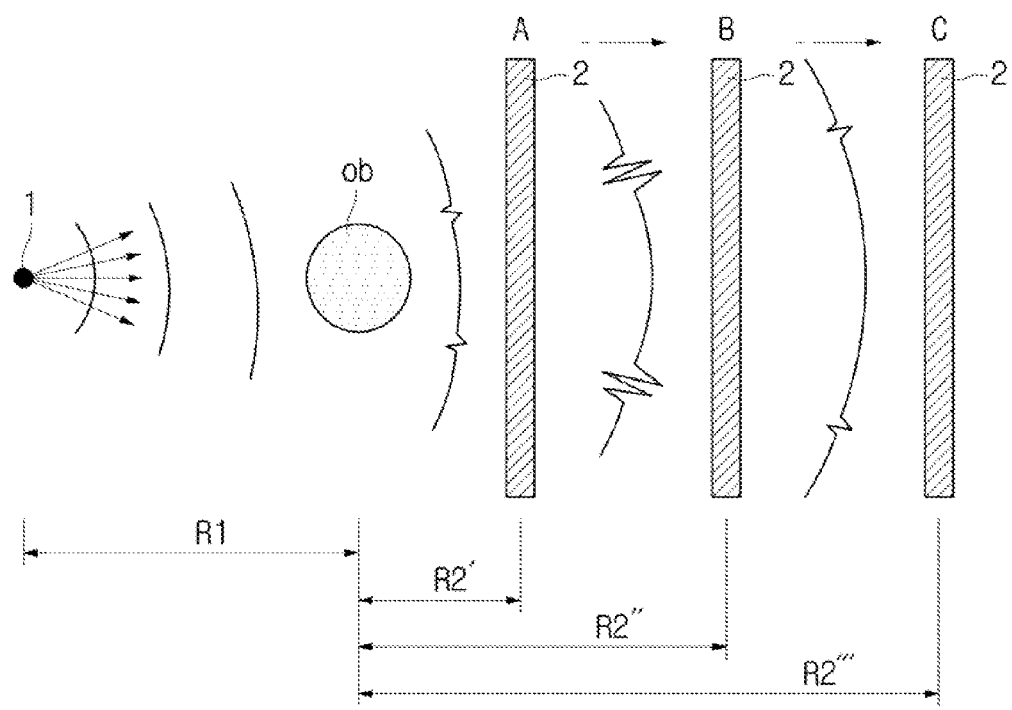
FIG. 5B is a view for describing a process of acquiring phase contrast images while moving an X-ray detector.

FIG. 5A is a view for describing a process of acquiring a phase contrast image, and FIG. 5B is a view for describing a process of acquiring phase contrast images while moving an X-ray detector.

According to the in-line phase contrast imaging, as illustrated in FIG. 5A, an X-ray detector 2 is positioned so as to be spaced by a distance of R2 apart from an object ob, and the object ob is disposed to be spaced by a distance of R1 apart from an X-ray source 1. Then, if X-ray beams are irradiated from the X-ray source 1 onto the object ob, the X-ray beams are transmitted through the object ob, and then detected by the X-ray detector 2 which is spaced apart by the distance of R2 from the object ob. Here, the distances R1 and R2 may be decided according to the properties of the object ob or according to environmental conditions for radiography.

The space between the object ob and the X-ray detector 2 is called a free space. While X-rays transmitted through the object ob are propagated in the free space, the phase shift of the X-rays is reflected in the intensities of the X-rays that are detected by the X-ray detector 2. In other words, when a free space is formed between an object and an X-ray detector, since the X-ray detector is spaced apart from the object by a predetermined distance, information about the phase shift of X-rays transmitted through the object is reflected in the intensities of X-rays to be detected.

However, in order to acquire a phase contrast image using the in-line phase contrast imaging, phase contrast information having different characteristics is needed. As shown in FIG. 5B, a degree at which a wave front is distorted depends on the propagation distances R2,' R2," and R2'" of X-ray beams in a free space. This means that a degree at which phase shift information is reflected in the intensities of X-ray beams vary according to the propagation distances R2,' R2," and R2'" of the X-ray beams. That is, the characteristics of the phase shift information that is reflected in the intensities of X-ray beams vary according to a distance R2 between the object ob and the X-ray detector 2. Accordingly, as illustrated in FIG. 5B, by moving the X-ray detector 2 to two or more different locations to detect X-ray beams at the different locations, a plurality of phase contrast image signals having different characteristics are acquired, and the phase contrast image signals are used to create a phase contrast image.

As described above, in order to acquire a phase contrast image signal, the X-ray detector 2 should be spaced by the distance of R2 apart from the object ob. Since at a point at which the X-ray detector 2 is located, an image of the object ob is enlarged at a magnification of (R1+R2)/R1, a large-scale X-ray detector corresponding to the magnification of (R1+R2)/R1 should be used in order to acquire an image signal corresponding to a Full Field Of View (Full FOV) image of the object ob. When radiography is carried out while moving the X-ray detector 2 to different locations according to the in-line phase contrast imaging, a larger-scale X-ray detector is required as the X-ray detector moves further from an object in order to acquire an image signal corresponding to a Full FOV image of the object ob.

As shown in FIG. 5B, as the X-ray detector 2 moves from a location A to a location B and from the location B to a location C, a magnification of an image of the object ob increases gradually from (R1+R2')/R1 to (R1+R2")/R1 and from (R1+R2'')/R1 to (R1+R2''')/R1. When the X-ray detector 2 is located at the location B, a larger-scale X-ray detector 2 is required than when the X-ray detector 2 is positioned at the location A in order to acquire an image signal corresponding to a Full FOV image of the object ob. When the X-ray detector 2 is positioned at the location C, a larger-scale X-ray detector 2 is required than when the X-ray detector 2 is positioned at the location B in order to acquire an image signal corresponding to a Full FOV image of the object ob.

Accordingly, an X-ray imaging apparatus according to an exemplary embodiment positions an X-ray collimator in front of an X-ray detector to focus X-ray beams onto a predetermined area. Therefore, an image signal can be acquired which corresponds to a Full FOV image of an object using an X-ray detector having a small size.

Figure 6:
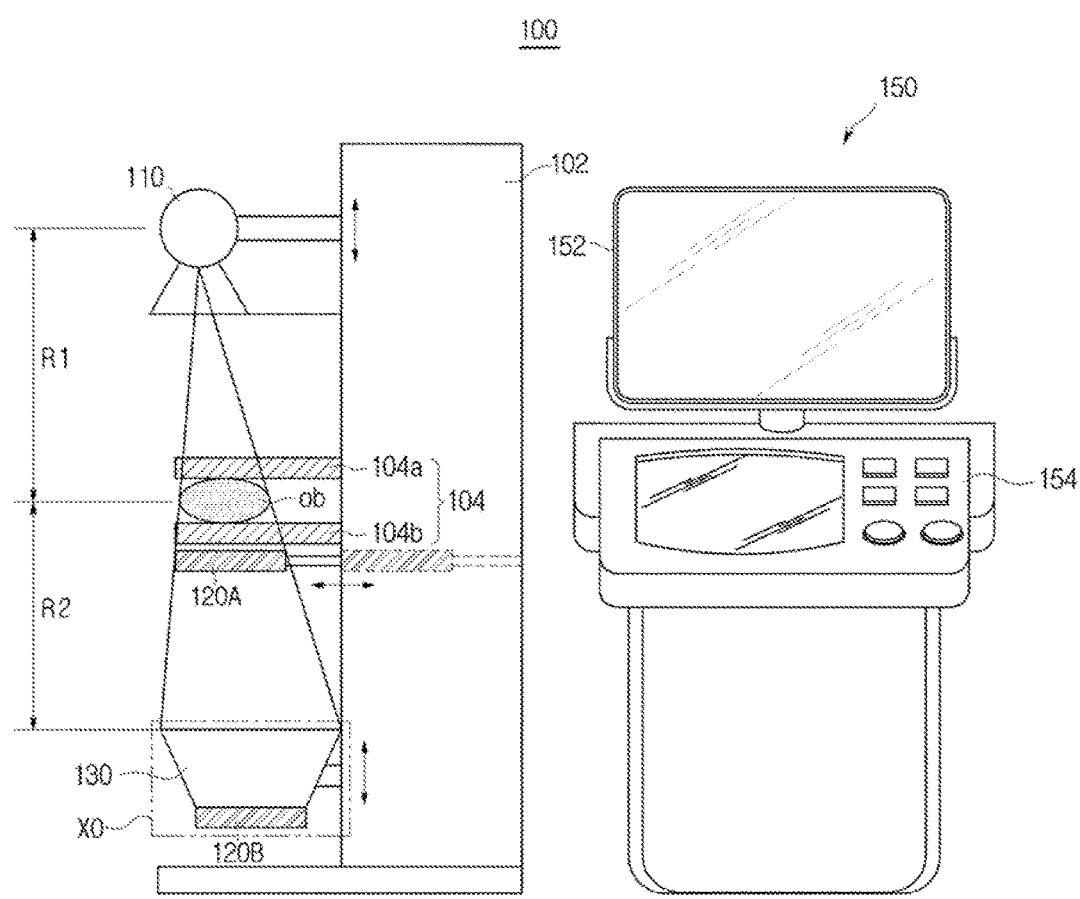
FIG. 6 illustrates an external appearance of an X-ray imaging apparatus.
Figure 7:
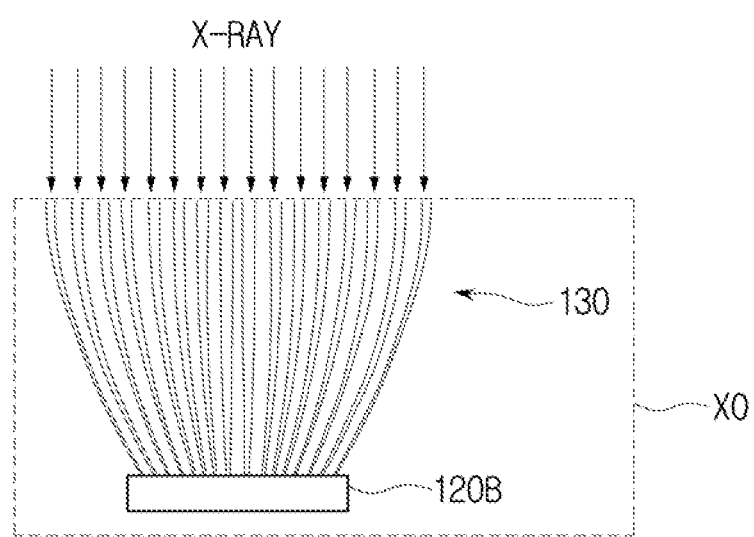
FIG. 7 is a view for describing a process of focusing and detecting X-ray beams.

FIG. 6 illustrates an external appearance of an X-ray imaging apparatus and FIG. 7 is a view for describing a process of focusing and detecting X-ray beams.

Referring to FIG. 6, an X-ray imaging apparatus 100 includes an X-ray source 110 to generate X-ray beams and irradiate the X-ray beams onto an object ob, a first X-ray detector 120A located adjacent to the object ob to detect an X-ray signal transmitted through the object ob, an X-ray obtainer XO including an X-ray collimator 130 which is spaced apart from the object ob by a predetermined distance R2 to focus the X-ray signal transmitted through the object ob, and a second X-ray detector 120B to detect the X-ray signal focused by the X-ray collimator 130, and a host 150 to receive various information associated with radiography and to display the results of radiography. The host can be, for example, a device which processes the radiography results.

The X-ray source 110 and the X-ray obtainer XO are connected to a housing 102 such that they can move in an up and down direction. The first X-ray detector 120A is movable in a left and right direction such that it can be located close to the object ob and then inserted into the housing 102.

The object ob may be fixed by a fixing assembly 104. The fixing assembly 104 may include a support 104b to support the object ob and a pressure paddle 104a to press the object ob.

If the object ob is an object such as a breast which consists of soft tissue, it is necessary to press and fix the object ob using the fixing assembly 104; however, there are objects that do not need to be pressed or fixed upon radiography. If the X-ray imaging apparatus 100 is dedicated to photographing objects which do not to be pressed or fixed upon radiography, the X-ray imaging apparatus 100 does not need to include fixing assembly 104 or the X-ray imaging apparatus 100 may include only the support 104b of the fixing assembly 104 and not the pressure paddle 104a.

The object ob may be a living body including a human body, or an arbitrary object through which X-rays can be transmitted and the inside of which can be visualized.

By moving the X-ray source 110 in the up and down direction, a distance R1 between the X-ray source 110 and the object ob can be adjusted, and by moving the X-ray obtainer XO in the up and down direction, a distance R2 between the object ob and the X-ray obtainer XO (more exactly, between the object ob and the X-ray collimator 130) can be adjusted.

After the distance R1 between the X-ray source 110 and the object ob is appropriately set, the X-ray source 110 is fixed at a location corresponding to the distance R1, the first X-ray detector 120A is positioned adjacent to the object ob, and then radiography of the object ob is carried out. In the following description, for convenience of description, the operation of irradiating X-ray beams onto the object ob to detect an X-ray signal transmitted through the object ob using the first X-ray detector 120A is referred to as "first radiography". After the first radiography is carried out, the first X-ray detector 120A that has detected the X-ray signal transmitted through the object ob moves to the right to be inserted into the housing 102.

After the distance R1 between the X-ray source 110 and the object ob is fixed, the X-ray obtainer XO moves to a location corresponding to the distance R2 to the object ob, and then radiography of the object ob is carried out. In the following description, for convenience of description, the operation of irradiating X-ray beams from the X-ray source 110 toward the object ob to detect an X-ray signal transmitted through the object ob which is then focused using the X-ray obtainer XO which is spaced by the distance R2 apart from the object ob, is referred to as "second radiography".

As described above, since an image of the object ob is enlarged at a magnification of (R1+R2)/R1 when X-ray beams are transmitted through the object ob are detected by an X-ray detector which is spaced apart from the object ob by a predetermined distance R2, a large-scale X-ray detector corresponding to the magnification of (R1+R2)/R1 should be used in order to acquire an image signal corresponding to a Full Field Of View (Full FOV) image of the object ob.

However, according to the current exemplary embodiment, as illustrated in FIGS. 6 and 7, by locating the X-ray collimator 130 in front of the second X-ray detector 120B that detects an X-ray signal transmitted through an object ob, the X-ray signal transmitted through the object ob is focused on a predetermined area by the X-ray collimator 130 before arriving at the second X-ray detector 120B so that an image signal corresponding to a Full FOV image of the object ob can be acquired by the second X-ray detector 120B which is small size in size.

As illustrated in FIG. 7, the X-ray collimator 130 changes the paths of X-ray beams transmitted through the object ob, and reduces the diameters of the X-ray beams, thereby focusing the X-ray beams to the second X-ray detector 120B on a predetermined area. The X-ray collimator 130 may be polycapillary optics, or any device capable of focusing X-ray beams that are transmitted through the object ob and then directed to the second X-ray detector 120B.

The current exemplary embodiment relates to a case in which the first X-ray detector 120A moves in the right direction and is inserted into the housing 102 before second radiography is carried out and after the first radiography is carried out. However, the first X-ray detector 120A may be removed or moved in a different way after the first radiography is carried out, as long as X-ray beams transmitted through the object ob can be incident on the second X-ray detector 120B without passing through the first X-ray detector 120A upon second radiography. For example, the first X-ray detector 120A may be removably attached to the housing 102. In this case, upon the first radiography, the first X-ray detector 120A may be attached to the housing 102 at a location adjacent to the object ob, and after the first radiography is carried out, the first X-ray detector 120A may be detached (removed) from the housing 102, and then second radiography may be carried out.

Alternatively, the first X-ray detector 120A may be designed to be bendable at a predetermined angle or more. In this case, upon performing the first radiography, the first X-ray detector 120A is located adjacent to the object ob, and after the first radiography is carried out, the first X-ray detector 120A may be bent in a predetermined direction and at a predetermined angle at which the first X-ray detector 120 will not influence the second radiography. Then the second radiography may be carried out. For example, referring to FIG. 6, the first X-ray detector 120A may be bent 90 degrees in a right and down direction, and then second radiography may be carried out.

After the first X-ray detector 120A and the second X-ray detector 120B detect and output the X-ray signals transmitted through the object ob, an image processor 140 (see FIG. 9) creates a phase contrast image and an absorption image about the object ob based on the detected X-ray signals. The image processor 140 may be included in the host 150 that controls the overall operation of the X-ray imaging apparatus 100, however, the location of the image processor 140 is not limited to this exemplary embodiment.

The host 150 may include a display 152 to display the phase contrast image and the absorption image of the object ob, created by the image processor 140. The host 150 may also include an input unit 154 to allow a user to input commands regarding the operations of the X-ray imaging apparatus 100.

Figure 8:
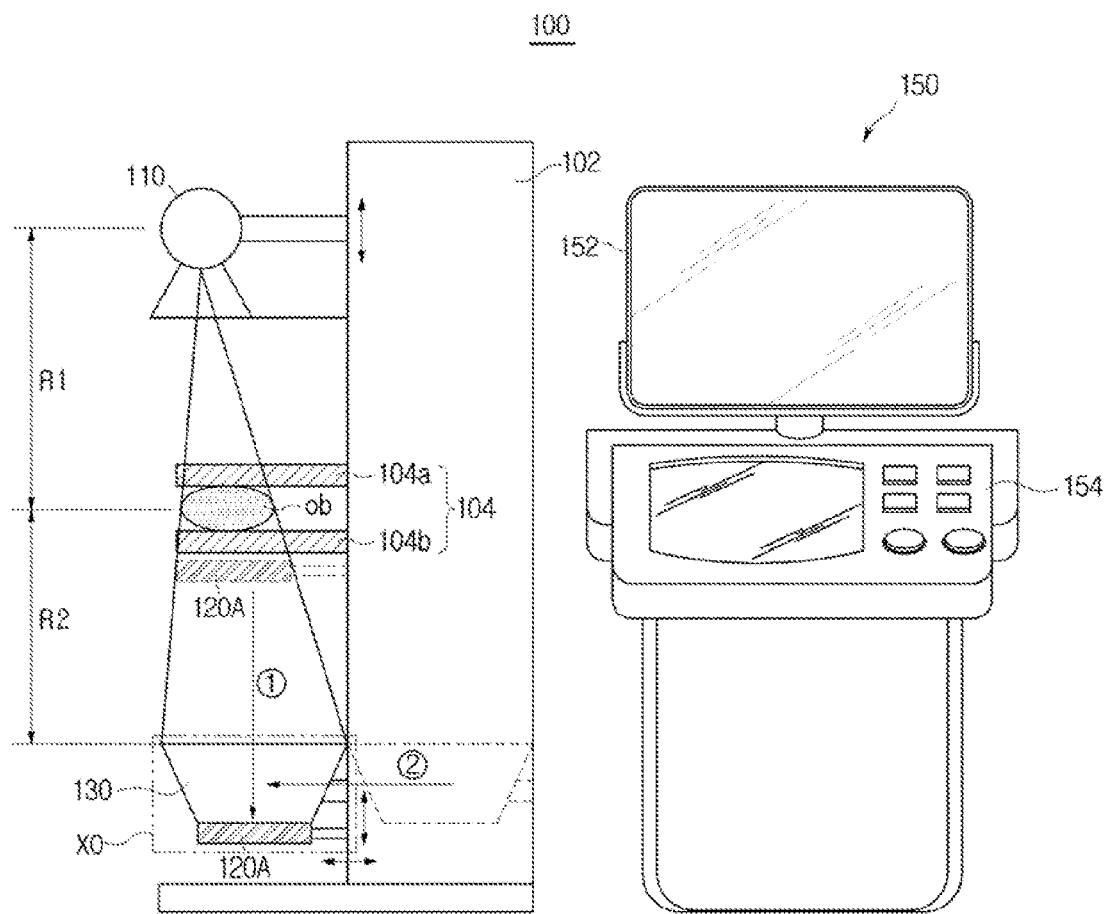
FIG. 8 illustrates an external appearance of an X-ray imaging apparatus.

Descriptions of the external appearance of the X-ray imaging apparatus 100 have been given with reference to FIGS. 6 and 7. In the example described in FIG. 6, the X-ray imaging apparatus 100 includes two X-ray detectors 120A and 120B, however, the X-ray imaging apparatus 100 may include a single X-ray detector 120A, which is illustrated in FIG. 8. In the example shown in FIG. 8, the X-ray detector 120A is attached to the housing 102 and is movable in an up and down direction. When the X-ray detector 120A is positioned adjacent to the object ob, first radiography is carried out, and then the X-ray detector 120A moves downward (in a direction indicated by an arrow ①). Then, the X-ray collimator 130 that has been inserted into the housing 102 moves in the left direction (in a direction indicated by an arrow ②), and is coupled with the X-ray detector 120A.

The X-ray detector 120A is designed to be movable in the left and right direction so that the upper surface (a surface contacting the X-ray collimator 130) of the X-ray detector 120A can accurately match the lower surface of the X-ray collimator 130. The X-ray detector 120A and the X-ray collimator 130 are coupled to form the X-ray obtainer XO, and the X-ray obtainer XO into which the X-ray detector 120A and the X-ray collimator 130 are integrated may be movable in the up and down direction with respect to the housing 102. That is, the X-ray detector 120A which is coupled with the X-ray collimator 130 can move in the up and down direction.

If a distance R2 between the object ob and the X-ray obtainer XO, more specifically, between the object ob and the X-ray collimator 130 is appropriately set when the distance R1 between the X-ray source 110 and the object ob is fixed upon first radiography, the X-ray obtainer XO is fixed at a location corresponding to the distance R2, and then radiography (second radiography) of the object ob is carried out.

The external appearance of the X-ray imaging apparatus shown in FIG. 8 is different from the external appearance of the X-ray imaging apparatus shown in FIG. 6 in that the X-ray imaging apparatus 100 shown in FIG. 8 includes a single X-ray detector 120A that can move in an up and down and left and right direction. The remaining components of the X-ray imaging apparatus shown in FIG. 8 are the same as the corresponding components of the X-ray imaging apparatus shown in FIG. 6, and accordingly, further descriptions thereof will be omitted.

Figure 9:
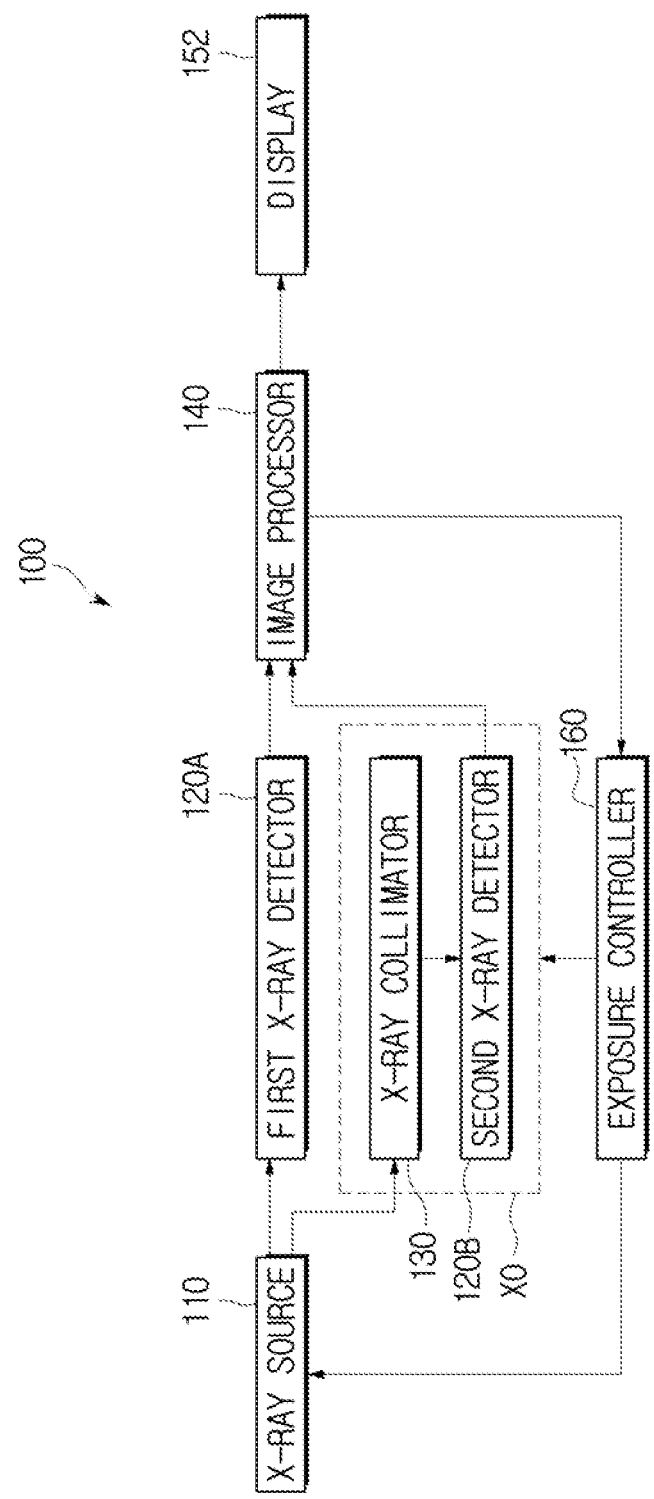
FIG. 9 is a block diagram of an X-ray imaging apparatus.

FIG. 9 is a block diagram of an X-ray imaging apparatus.

Referring to FIG. 9, an X-ray imaging apparatus 100 includes an X-ray source 110 which generates X-ray beams and irradiates the X-ray beams onto an object ob, a first X-ray detector 120A located adjacent to the object ob to detect an X-ray signal transmitted through the object ob, an X-ray obtainer XO including an X-ray collimator 130 which is spaced apart from the object ob by a predetermined distance R2 to focus an X-ray signal transmitted through the object ob, and a second X-ray detector 120B to detect the X-ray signal focused by the X-ray collimator 130, The X-ray imaging apparatus 100 also includes an image processor 140 to create a phase contrast image and an absorption image about the object based on the X-ray signals acquired by the first X-ray detector 120A and the second X-ray detector 120B, Further, the X-ray imaging apparatus 100 also includes a display 140 which displays the phase contrast image and the absorption image about the object ob, and an exposure controller 160 to set and control conditions that are to be applied to the radiography based on an image signal acquired by pre-shot imaging, such as pre-shot X-ray imaging.

Since the second X-ray detector 120B is spaced apart from the object ob by a predetermined distance R2, an X-ray signal detected by the second X-ray detector 120B includes phase shift information of X-ray beams. Accordingly, a phase contrast image can be created using pixel-based signals output from the first and second X-ray detectors 120A and 120B. In the following exemplary embodiment, signals regarding the intensities of X-ray beams output from the first X-ray detector 120A and the second X-ray detector 120B are defined as phase contrast image signals.

Hereinafter, the operations of the individual components of the X-ray imaging apparatus 100 will be described in detail.

The X-ray source 110 receives a supply voltage from a power supply (not shown) to generate X-ray beams. The energy of the X-ray beams can be controlled according to a tube voltage, and the intensities or dose of the X-ray beams can be controlled by tube current and an X-ray exposure time.

When X-ray beams, which will be irradiated, have a predetermined energy band, the predetermined energy band may be defined by upper and lower limits. The upper limit of the predetermined energy band, that is, a maximum energy of X-ray beams to be irradiated may be adjusted by the magnitude of a tube voltage. The lower limit of the predetermined energy band, that is, a minimum energy of X-ray beams to be irradiated, may be adjusted by a filter included in or provided outside of the X-ray source 110. By filtering out a low energy band of X-ray beams using the filter, an average energy of X-ray beams to be irradiated may increase.

In order to create a phase contrast image, X-ray beams which will be irradiated must have the same phase. X-ray beams having the same phase are called spatial coherent X-ray beams. Accordingly, the X-ray source 110 may be embodied as a device capable of generating an X-ray laser, high-order harmonics, or synchrotron radiation having high spatial coherence. Alternatively, the X-ray source 110 may be embodied as a point source in which a focal spot size is reduced using a general X-ray tube.

Figure 10:
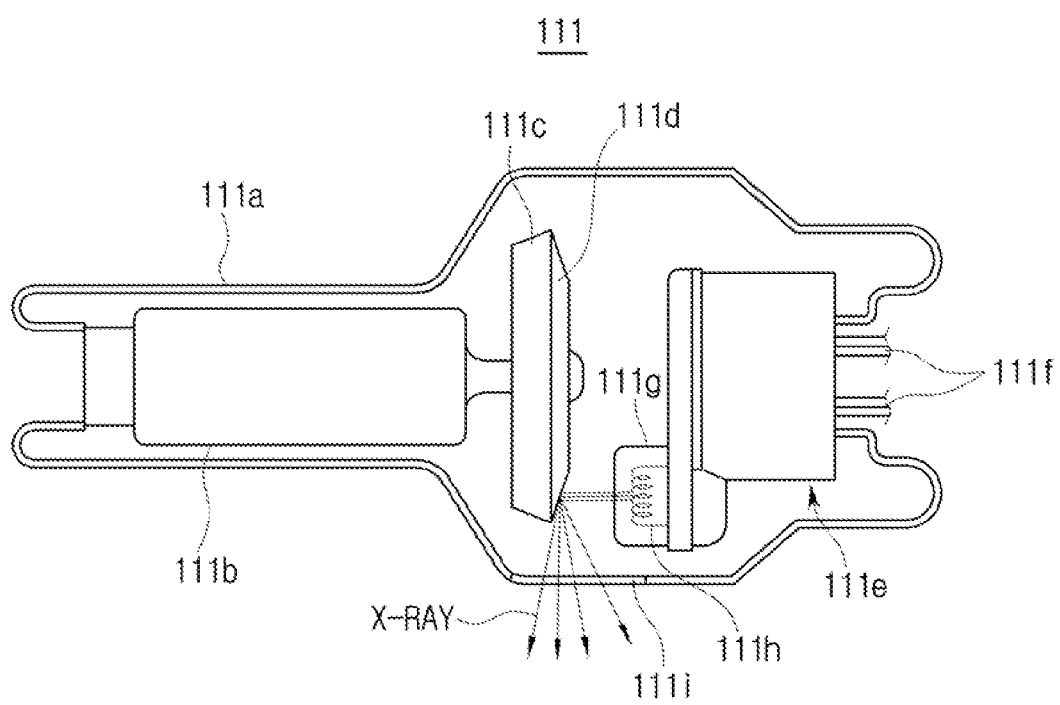
FIG. 10 illustrates an internal structure of an X-ray tube included in an X-ray source illustrated in FIG. 6.

FIG. 10 illustrates an internal structure of an X-ray tube included in the X-ray source 110 illustrated in FIG. 6.

As described above, according to an exemplary embodiment, the X-ray imaging apparatus 100 may irradiate spatial coherent X-ray beams using a general X-ray tube.

Referring to FIG. 10, the X-ray source 110 may include an X-ray tube 111. The X-ray tube 111 may be embodied as a two-electrode vacuum tube including an anode 111c and a cathode 111e. The cathode 111e includes a filament 111h and a focusing electrode 111g for focusing electrons. The focusing electrode 111g is also called a focusing cup. The inside of a glass tube 111a is evacuated to create a high vacuum state of about 10 mm Hg, and the filament 111h of the cathode 111e is heated to a high temperature, to generate thermoelectrons. The filament 111h may be a tungsten filament, and the filament 111h may be heated by applying current to electrical leads 111f which are connected to the filament 111h.

The anode 111c may be made of copper, and a target material 111d is applied to the surface of the anode 111c facing the cathode 111e, The target material 111d may be a high-resistance material, such as, chromium (Cr), iron (Fe), cobalt (Co), nickel (Ni), tungsten (W), or molybdenum (Mo). The higher the melting point of the target material 111d, the smaller the focal spot size. The focal spot is an effective focal spot. The target material 111d is formed to have a slope which is inclined at a predetermined angle, and the smaller the predetermined angle, the smaller the focal spot size.

When a high voltage is applied between the cathode 111e and the anode 111c, thermoelectrons are accelerated and collide with the target material 111d of the anode 111c, thereby generating X-ray beams. The X-ray beams are irradiated outside of the X-ray tube 111 through a window 111i. The window 111i may be a beryllium (Be) thin film. Also, a filter (not shown) for filtering a specific energy band of X-rays may be provided on the front or rear side of the window 111i.

Also, the target material 111d may be rotated by a rotor 111b. When the target material 111d rotates, the heat accumulation rate may increase ten times per unit area and the focal spot size may be reduced, as compared to when the target material 111d is fixed.

The voltage that is applied between the cathode 111e and the anode 111c of the X-ray tube 111 is called a tube voltage. The magnitude of a tube voltage may be expressed as a crest value (kVp). When the tube voltage increases, the velocity of thermoelectrons increases accordingly. Then, energy, such as energy of photons, of the X-ray beams that are generated when the thermoelectrons collide with the target material 111d also increases. A current flowing through the X-ray tube 111 is called tube current, and can be expressed as an average value (mA). When the tube current increases, the number of thermoelectrons emitted from the filament 111h increases. As a result, a dose of X-ray beams (that is, the number of X-ray photons) that are generated when the thermoelectrons collide with the target material 111d increases.

In summary, the energy of the X-ray beams can be controlled by adjusting a tube voltage. Also, a dose or intensities of X-ray beams can be controlled by adjusting tube current and an X-ray exposure time. When X-ray beams to be irradiated have a predetermined energy band, the predetermined energy band may be defined by upper and lower limits. The upper limit of the predetermined energy band, that is, a maximum energy of X-ray beams to be irradiated may be adjusted by the magnitude of a tube voltage. The lower limit of the predetermined energy band, that is, a minimum energy of X-ray beams to be irradiated may be adjusted by a filter. By filtering out a low energy band of the X-ray beams using the filter, an average energy value of the X ray beams to be irradiated may increase.

In order for the first X-ray detector 120A and the second X-ray detector 120B to acquire phase contrast image signals for a plurality of energy bands, the X-ray source 111 may irradiate polychromatic X-rays, and the energy bands of the polychromatic X-rays may be defined by upper and lower limits.

According to an exemplary embodiment, the X-ray imaging apparatus 100 may irradiate spatial coherent X-ray beams using a general X-ray tube. For example, by adjusting the focal spot size to several micrometers or several tens of micrometers, spatial coherent X-ray beams can be generated. The higher the melting point and rotation speed of the target material 111d, and the more gradual the slope of the target material 111d, the smaller the focal spot size. In addition, the focal spot size may vary according to a tube voltage, tube current, the size of the filament 111h, the size of the focusing electrode 111e, a distance between the anode 111c and the cathode 111e, etc. By adjusting controllable ones among the above-mentioned conditions to reduce the focal spot size to several or several tens of micrometers, spatial coherent X-ray beams can be generated. However, the focal spot size may also vary according to the properties of an object.

Since the first X-ray detector 120A and the second X-ray detector 120B have the same structure and function, in the following description, the first X-ray detector 120A and the second X-ray detector 120B will be referred to as X-ray detector 120 except for a case in which the first and second X-ray detectors 120A and 120B should be distinguished from each other.

The X-ray detector 120 detects X-ray beams transmitted through the object ob, and converts the detected X-ray beams into electrical signals to acquire phase contrast image signals.

Each X-ray detector 120 can be classified according to its configuration, a method of converting detected X-ray beams into electrical signals, and a method of acquiring image signals.

The X-ray detector 120 is classified into a mono type device or a hybrid type device according to its material configuration.

If the X-ray detector 120 is a mono type device, a part of the device for detecting X-ray beams and generating electrical signals, and a part of the device for reading and processing the electrical signals may be semiconductors made of the same material, or may be manufactured by a single process. In this case, the X-ray detector 120 may be a Charge Coupled Device (CCD) or a Complementary Metal Oxide Semiconductor (CMOS) which is a light receiving device.

If the X-ray detector 120 is a hybrid type device, a part of the device for detecting X-ray beams and generating electrical signals, and a part of the device for reading and processing the electrical signals may be made of different materials, or may be manufactured by different processes. For example, X-ray beams can be detected using a photo-diode or a light receiving device such as cadmium zinc telluride (CdZnTe), and reading and processing electrical signals using a CMOS Read Out Integrated Circuit (CMOS ROIC), of detecting X-ray beams using a strip detector, and reading and processing electrical signals, and of using an amorphous silicon (a-Si) or an amorphous selenium (a-Se) flat panel system.

The X-ray detector 120 may use a direct conversion mode and an indirect conversion mode for converting X-ray beams into electrical signals.

In the direct conversion mode, if X-ray beams are irradiated, electron-hole pairs are temporarily generated in a light receiving device, electrons move to an anode and holes move to a cathode by an electric field applied to both terminals of the light receiving device. The X-ray detector 120 then converts the movement of the electrons and holes into an electrical signal. The light receiving device may be made of a-Se, CdZnTe, mercury iodide (HgI2), or PbI2.

In the indirect conversion mode, a scintillator is provided between a light receiving device and an X-ray source. If X-rays irradiated from an X-ray source react with the scintillator to emit photons having a wavelength of a visible light region, the light receiving device detects the photons, and converts the photons into an electrical signal. The light receiving device may be made of a-Si, and the scintillator may be a gadolinium oxysulfide (GADOX) scintillator of a thin film type, or a thallium doped cesium iodide (CSI (TI)) of a micro pillar type or a needle type.

The X-ray detector 120 may use a charge integration mode of storing charges for a predetermined time period and then acquire a signal from the stored charges, or may use a photon counting mode of counting the number of photons having an energy higher than threshold energy whenever a signal is generated by single X-ray photons, according to a method of acquiring image signals.

The material configuration of the X-ray detector 120 and the signal conversion method of the X-ray detector 120 are not limited to any specific embodiment, however, for convenience of description, in an exemplary embodiment which will be described below, it is assumed that the X-ray detector 120 uses the direct conversion mode of acquiring electrical signals directly from X-ray beams, and the X-ray detector 120 is a hybrid type in which a light receiving device for detecting X-ray beams is integrated with a read circuit chip.

Figure 11:
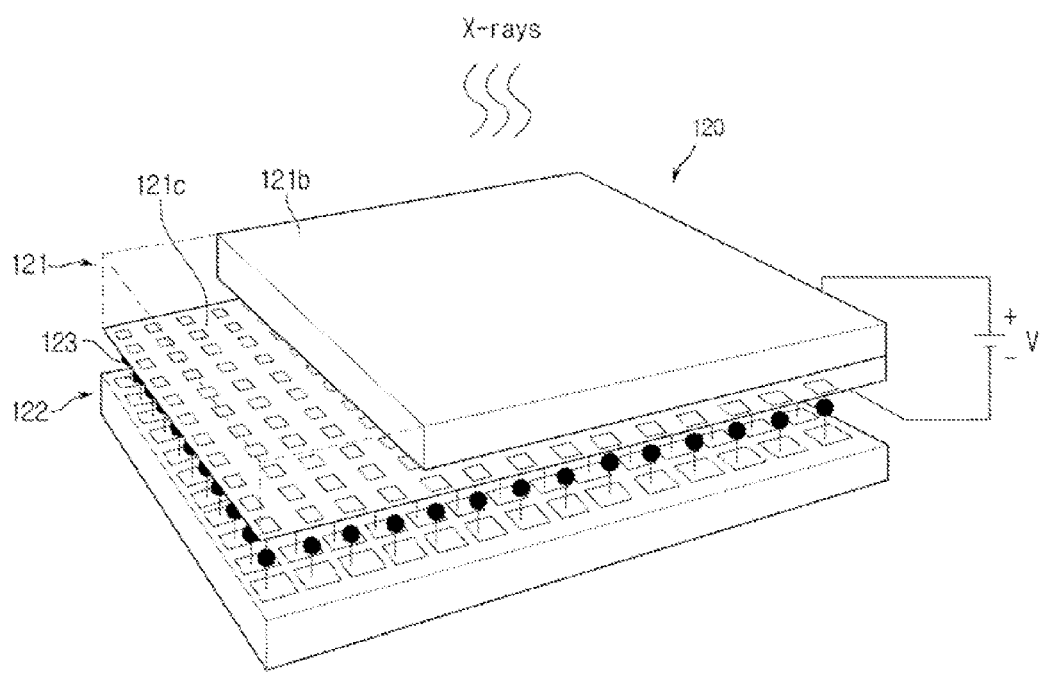
FIG. 11 is a perspective view illustrating a structure of an X-ray detector in an X-ray imaging apparatus.

FIG. 11 is a perspective view illustrating a structure of the X-ray detector 120 included in the X-ray imaging apparatus 100.

Referring to FIG. 11, the X-ray detector 120 includes a light receiving device 121 to detect X-ray beams and convert the X-ray beams into electrical signals, and a read circuit 122 to read out the electrical signals. The read circuit 122 is in the form of a two-dimensional (2D) pixel array including a plurality of pixel areas. The light receiving device 121 may be made of a single crystal semiconductor material in order to ensure high resolution, high response speed, and a high dynamic area even under conditions of low energy and small X-ray dosage. The single crystal semiconductor material may be Ge, cadmium telluride (CdTe), CdZnTe, or gallium arsenide (GaAs).

The light receiving device 121 may be in the form of a PIN photodiode. The PIN photodiode is fabricated by bonding a p-type layer 121*c* in which p-type semiconductors are arranged in the form of a 2D pixel array on the lower surface of an n-type semiconductor substrate 121*b* which has a high resistance. The read circuit 122, which is fabricated according to a CMOS process, is coupled with the light receiving device 121 in units of pixels. The CMOS read circuit 122 and the light receiving device 121 may be coupled by a Flip-Chip Bonding (FCB) method. More specifically, the CMOS read circuit 122 and the light receiving device 121 may be coupled by forming bumps 123 with lead (Pb), tin (Sn), indium (In), or the like, and then performing reflowing, applying heat, and then compressing. However, the X-ray detector 120 is not limited to this structure.

The X-ray imaging apparatus 100 may acquire phase contrast image signals for a plurality of different energy bands in order to create a phase contrast image of an object ob. In order for the X-ray imaging apparatus 100 to acquire phase contrast image signals for a plurality of different energy bands, the X-ray source 110 may irradiate a plurality of X-ray beams having different energy bands independently, or the X-ray source 110 may irradiate a wide band of X-ray beams including a plurality of energy bands at a single time, and then the X-ray detector 120 may detect the wide band of X-ray beams and divide the wide band of X-ray beams according to the plurality of energy bands.

Figure 12:
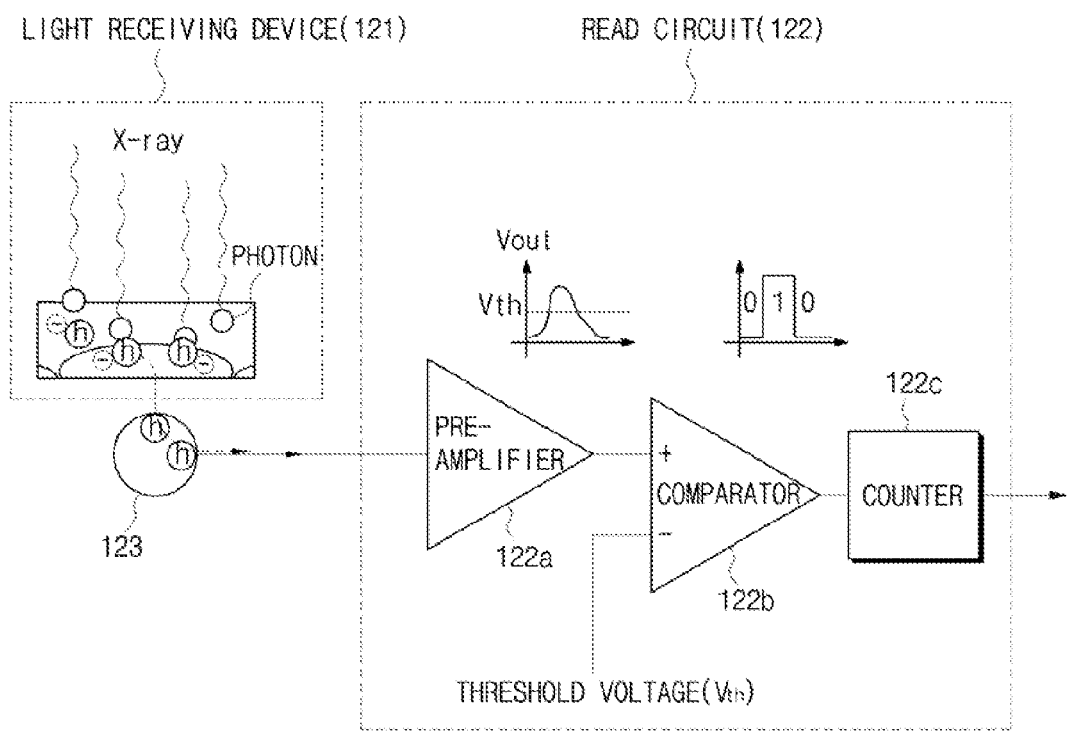
FIG. 12 illustrates a structure of a pixel area of the X-ray detector illustrated in FIG. 11.

FIG. 12 illustrates a structure of a pixel area of the X-ray detector 120 illustrated in FIG. 11.

As illustrated in FIG. 12, when X-ray photons are incident on the light receiving device 121, electrons that have been in a valence band receive the energy of the photons so that their total energy exceeds a bandgap energy difference to be excited on a conduction band. Thus, electron-hole pairs are created in a depletion region.

When metal electrodes are respectively formed on the p-type layer 121*c* and the n-type substrate 121*b* (see FIG. 11) of the light receiving device 121, and a reversed bias voltage is applied between the p-type layer 121*c* and the n-type substrate 121*b*, the electrons in the electron-hole pairs created in the depletion region move to the n-type region, and the holes move to the p-type region. The holes moved to the p-type region are input to the read circuit 122 through the bumps 123 (see FIG. 11) so that the read circuit 122 can read electrical signals generated by the photons. However, the electrons may be input to the read circuit 122 to generate electrical signals according to the structure of the light receiving device 122, an applied voltage, etc.

The read circuit 122 may be in the form of a 2D pixel array corresponding to the p-type semiconductor of the light receiving device 121, and reads out an electrical signal in a unit of a pixel. If charges are input from the light receiving device 121 to the read circuit 122 through the bumps 123, a pre-amplifier 122*a* of the read circuit 122 charges an input charge generated from a photon, and outputs a voltage signal corresponding to the input charge.

The voltage signal output from the pre-amplifier 122*a* is transferred to a comparator 122*b*. The comparator 122*b* compares the voltage signal to a threshold voltage that can be controlled by an external device, and outputs a pulse signal of "1" or "0," according to the result of the comparison, to a counter 122*c*. The counter 122*c* counts the number of signals having a value of "1", and outputs the count value as a digital image signal. Then, image signals corresponding to individual pixels are combined so that an X-ray image of the object is created.

Here, the threshold voltage corresponds to threshold energy E, and in order to count the number of photons having higher energy than the threshold energy E, a threshold voltage corresponding to the threshold energy E is input to the comparator 122*b*. The threshold energy can correspond to a threshold voltage because an electrical signal (a voltage) that is generated by the light receiving device 121 depends on the energy of photons. A threshold voltage corresponding to a desired threshold energy can be calculated using a relationship between the energy of the photons and a voltage to be generated. In an exemplary embodiment, which will be described below, inputting threshold energy to the X-ray detector 120 may also mean inputting a threshold voltage corresponding to threshold energy.

Figure 13:
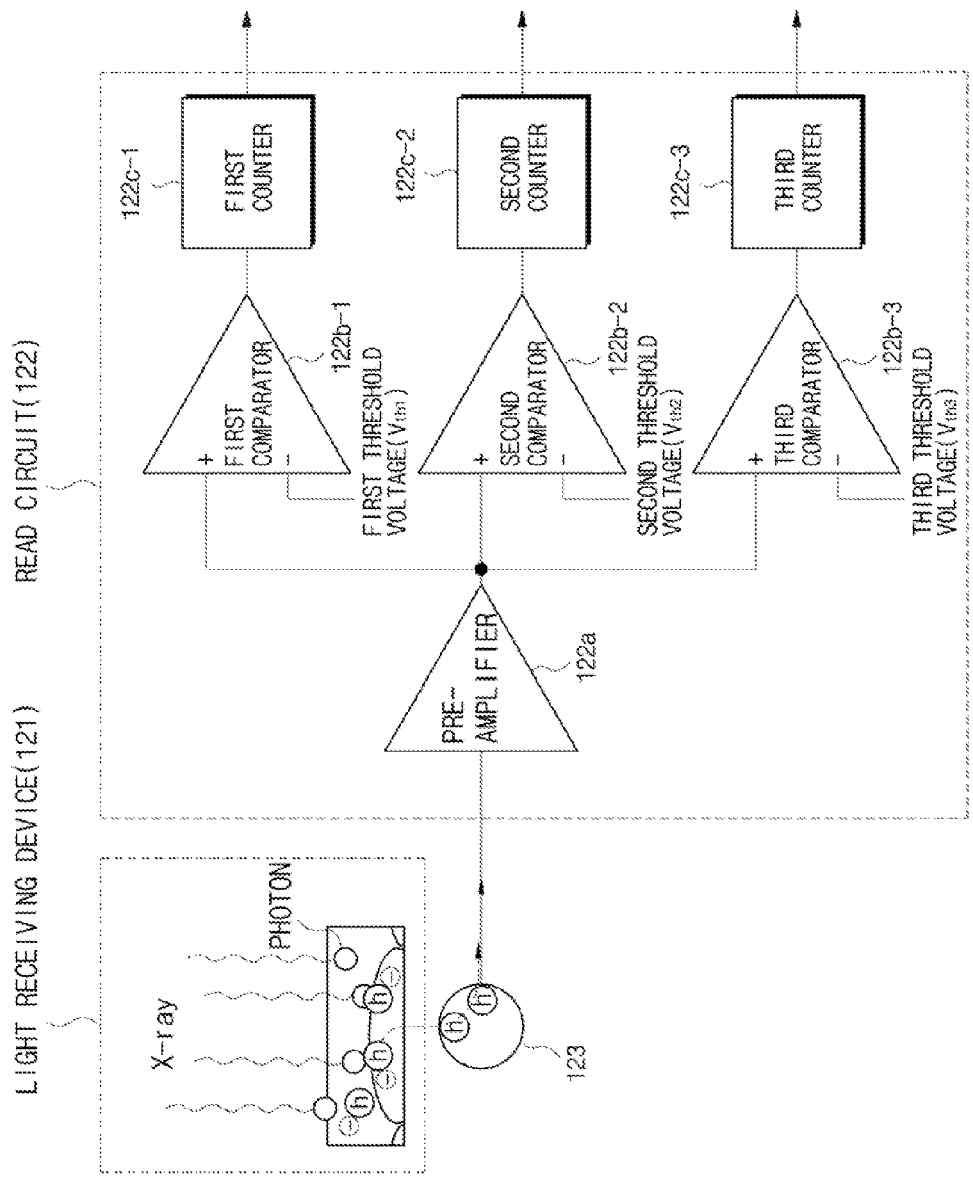
FIG. 13 illustrates a structure of a pixel area of an X-ray detector capable of dividing detected X-ray signals according to a plurality of energy bands.

FIG. 13 illustrates a structure of a pixel area of an X-ray detector 120 capable of dividing detected X-ray beams into a plurality of energy bands.

According to an exemplary embodiment, in order for the X-ray imaging apparatus 100 to acquire phase contrast image signals having different characteristics according to energy bands, the X-ray source 110 irradiates a wide band of X-ray beams including a plurality of energy bands at a single time. The X-ray detector 120 detects the wide band of X-ray beams, and divides the wide band of X-ray beams according to the plurality of energy bands.

As illustrated in FIG. 13, a plurality of comparators and a plurality of counters are provided to count the number of photons for each energy band. In FIG. 13, three comparators and three counters are provided, however, a different number of comparators and a different number of counters may be provided according to the number of energy bands to be divided.

Referring to FIG. 13, when an electron or a hole generated by a single photon is input into a pre-amplifier 122a and then output as a voltage signal, the voltage signal is input to three comparators, a first comparator 122b-1, a second comparator 122b-2, and a third comparator 122b-3. Then, a first threshold voltage $V_{th1}$, a second threshold voltage $V_{th2}$, and, a third threshold voltage $V_{th3}$ are applied to the respective first comparator 122b-1, second comparator 122b-2, and third comparator 122b-3. The first comparator 122b-1 compares the voltage signal to the first threshold voltage $V_{th1}$, and a first counter 122c-1 counts the number of photons that have generated a higher voltage than the first threshold voltage $V_{th1}$. In the same way, a second counter 122c-2 counts the number of photons that have generated a higher voltage than the second threshold voltage $V_{th2}$, and a third counter 122c-3 counts the number of photons that have generated a higher voltage than the third threshold voltage $V_{th3}$.

Accordingly, since the X-ray detector 120 is embodied as a Photon Counting Detector (PCD) capable of dividing detected X-ray beams according to a plurality of energy bands, phase contrast image signals having different characteristics can be acquired through a single radiography operation without having to carry out radiography several times while moving the X-ray detector 120. Here, the different characteristics of the phase contrast image signals are not characteristics according to the distance between an object and the X-ray detector 120, but are characteristics according to energy bands to which the phase contrast image signals belong.

According to an exemplary embodiment, the X-ray imaging apparatus 100 (see FIG. 6 or 8) uses the photon counting mode that can create X-ray images which have lower noise with a lower dose of X-rays, compared to the charge integration mode. After X-ray beams are irradiated a single time, the X-ray detector 120 divides detected X-ray beams according to a plurality of energy bands.

The image processor 140 (see FIG. 9) creates a phase contrast image and an absorption image of the object based on image signals, such as phase contrast signals, acquired by the first X-ray detector 120A and the second X-ray detectors 120B.

Figure 14:
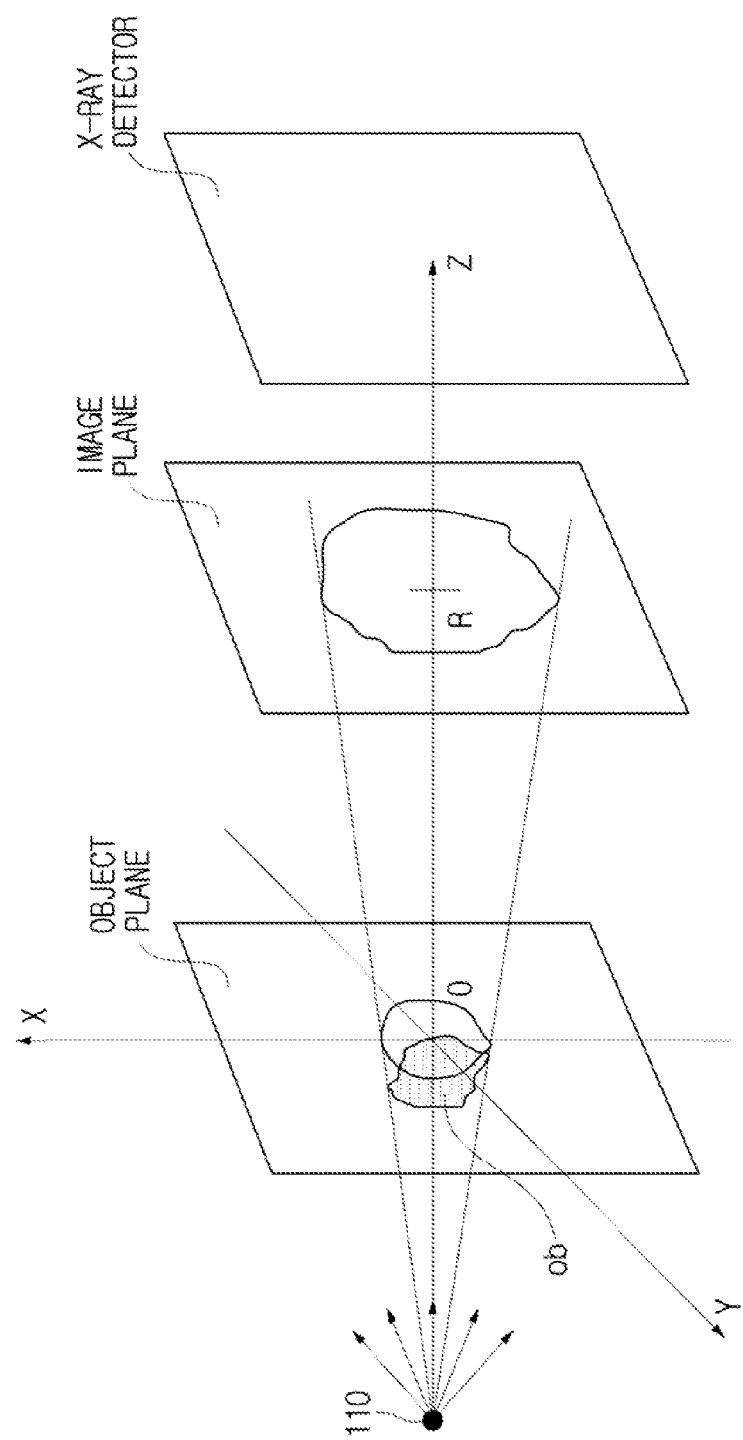
FIG. 14 geometrically illustrates the locations of an object and an X-ray detector in order to describe phase retrieval.

FIG. 14 geometrically illustrates the locations of an object and an X-ray detector in order to describe phase retrieval.

Hereinafter, a process in which the image processor 140 creates a phase contrast image will be described in detail with reference to FIGS. 9 and 14.

First, the image processor 140 performs phase retrieval on a phase contrast signal output from the X-ray detector 120. In order to perform the phase retrieval, a geometrical relationship as illustrated in FIG. 14 is used. Referring to FIG. 14, it is assumed that an object ob and the X-ray detector 120 are located in a 3-dimensional (3D) space defined by the x-, y-, and z-axes. The object ob is located on an object plane, and the X-ray detector 120 is located on an image plane. Here, the z-axis is an optical axis along which X-ray beams are propagated. The object plane is positioned at z=0, and the image plane is positioned at z=R.

Distributions in intensity I and phase Φ of a detected X-ray beam can be expressed in view of line integrals of a complex index of refraction, and the complex index n of refraction can be defined by Equation (1) below.

$$n(r)=1-\delta-i\beta, \quad [\text{Equation 1}]$$

where the imaginary part β represents absorption or attenuation of the X-ray beam, the real part δ represents phase shift with respect to a material of an object ob, n satisfies |n−1|<<1, and r is defined by (r⊥,z).

Accordingly, the distributions in intensity I and phase Φ of the X-ray beam can be defined by Equations (2) and (3) below.

$$I(r_\perp,0,\lambda)=\exp[-M(r_\perp,0,\lambda)] \quad [\text{Equation 2}]$$

where, $M(r_\perp,0,\lambda)=(4\pi/\lambda)\int_{-\infty}^{0}\beta(r_\perp,z',\lambda)dz'$.

$$\phi(r_\perp,0,\lambda)=-(2\pi/\lambda)\int_{-\infty}^{0}\delta(r_\perp,z',\lambda)dz', \quad [\text{Equation 3}]$$

where M represents absorption and attenuation of the X-ray beam. Dependencies of the imaginary part β and real part δ of the complex index n of refraction with respect to a wavelength λ can be expressed by Equations 4 and 5, below.

$$\beta(\lambda)=(\lambda/\lambda_0)^4\beta(\lambda_0). \quad [\text{Equation 4}]$$

$$\delta(\lambda)=(\lambda/\lambda_0)^2\delta(\lambda_0) \quad [\text{Equation 5}]$$

X-ray propagation from the object plane z=0 to the image plane z=R can be expressed by a Fresnel integral, and the Fresnel integral can approximate Equation (6) using a Transport of Intensity Equation (TIE).

$$(R\lambda/2\pi)[-\nabla^2\phi(r_\perp,0,\lambda)-\nabla\phi(r_\perp,0,\lambda)\cdot\nabla\ln I(r_\perp,0,\lambda)]=I(r_\perp,R,\lambda)/I(r_\perp,0,\lambda)-1 \quad [\text{Equation 6}]$$

In Equation (6), if the distribution in intensity of the X-ray beam on the object plane is not greatly different from the distribution in intensity of the X-ray beam on the image plane, the right side can be rewritten to ln [I(r⊥,R̃,λ)]−ln [I(r⊥,0,λ)].

Based on Equations (2) through (5), Equation (6) can be rewritten to Equation (7) as follows.

$$-\sigma^3 M(r_\perp,0,\lambda_0)+\gamma\sigma(-\nabla^2\phi)(r_\perp,0,\lambda_0)+\gamma\sigma^4\nabla\phi(r_\perp,0,\lambda_0)\cdot\nabla M(r_\perp,0,\lambda_0)=\ln[I(r_\perp,R,\lambda)], \quad \text{Equation (7)}$$

where $\sigma=\lambda/\lambda_0$, and $\gamma=R\lambda/2\pi$. For example, when the X-ray detector 120 divides phase contrast image signals according to three energy bands, that is, when phase contrast image signals correspond to three different wavelengths $\lambda_0$, $\lambda_1$, and $\lambda_2$, Equation (8) can be defined as follows.

$$A\begin{pmatrix} M(r_\perp,0,\lambda_0) \\ -\nabla^2\varphi(r_\perp,0,\lambda_0) \\ \nabla M\cdot\nabla\varphi(r_\perp,0,\lambda_0) \end{pmatrix}=\begin{pmatrix} F_0 \\ F_1 \\ F_2 \end{pmatrix} \quad [\text{Equation 8}]$$

where,

-continued $$A = \begin{pmatrix} -1 & \gamma_0 & \gamma_0 \\ -\sigma_1^3 & \sigma_1\gamma_1 & \sigma_1^4\gamma_1 \\ -\sigma_2^3 & \sigma_2\gamma_2 & \sigma_2^4\gamma_2 \end{pmatrix}.$$

In Equation 7, $F_i=\ln[I(r\perp,R,\lambda_i)]$, which corresponds to the right side, can be calculated using phase contrast image signals according to three energy bands output from the X-ray detector 120. That is, by using the intensities of X-ray beams for three energy bands. Accordingly, M representing the absorption and attenuation of the X-ray beam and a Laplacian phase distribution can be acquired by finding the value of Equation (8), and the phase distribution Φ can be retrieved using Poisson equation expressed as Equation (9) below.

$$-\nabla^2 \phi(r_\perp, 0, \lambda_0) = \Sigma A_{1j}^{-1} F_j \quad \text{[Equation 9]}$$

If the phase distribution Φ is retrieved, the complex index n of refraction is decided according to Equations (1), (2), and (3). The image processor 140 decides the complex index n of refraction according to the above-described process, and creates a phase contrast image of the object ob using the complex index n of refraction. The phase contrast image of the object ob clearly shows the outlines of materials constructing the object ob, and even small details.

Meanwhile, the image processor 140 may perform image calibration, such as flat field correction, noise reduction, etc., for improving the picture quality of the X-ray images, and the phase contrast image of the object ob, which is subject to image calibration, is displayed on the display 152.

Also, the image processor 140 can create an absorption image which does not include phase contrast information of X-ray beams. The image processor 140 may selectively create one or both of an absorption image and a phase contrast image as necessary, and display the created image(s) on the display 152. The image processor 140 may carry out radiography after moving the X-ray detector 120 towards the location of the object ob to create an absorption image. Also, the image processor 140 may create an absorption image using phase contrast image signals acquired after spacing the X-ray detector 120, by a predetermined distance apart from the object ob, to create a phase contrast image.

The exposure controller 160 (see FIG. 9) sets and controls conditions, such as various parameters, that are applied to the radiography based on an image signal acquired by pre-shot imaging so that optimal X-ray beams can be irradiated onto an object ob according to the properties of the object ob during radiography.

The pre-shot imaging is carried out prior to performing radiography in order to set conditions for radiography according to the properties of an object ob. The pre-shot imaging may be carried out with a low dose of X-rays by adjusting a tube current and an X-ray exposure time. The conditions that are controlled by the exposure controller 160 include conditions regarding generation and irradiation of X-ray beams, and conditions regarding distances between the X-ray source 110, the object ob, and the X-ray obtainer XO.

The exposure controller 160 may set conditions regarding the generation of X-rays, for example, conditions such as a tube voltage, tube current, target materials of both electrodes, an exposure time, a distance between an anode and a cathode, and a filter type. In order to optimize the above-mentioned conditions for the object ob, the exposure controller 160 may analyze a pre-shot image of the object ob to set conditions which are optimized for the properties of the object ob. To do this, the exposure controller 160 may receive an image signal from the X-ray detector 120, or may receive an image-processed image signal from the image processor 140. Also, as illustrated in FIG. 6, when the object ob is pressed and fixed by the fixing assembly 104, the exposure controller 160 may receive information about a distance between the pressure paddle 104a and the support 104b to set a condition at which a thickness characteristic of the object ob is reflected.

The exposure controller 160 may also set and control a distance R1 between the X-ray source 110 and the object ob and may set a distance R2 between the object ob and the X-ray obtainer XO. In order to set and control the distance, the exposure controller 160 may analyze a pre-shot image in order to detect the properties of materials constructing the object ob, and in order to appropriately set distances R1 and R2 based on a focal spot size of the X-ray source 110, the properties of the object ob including the thickness of the object ob, FOV of X-ray beams, etc.

As illustrated in FIGS. 6 and 8, in the case where the X-ray source 110 and the X-ray obtainer XO can move in the up and down direction along the housing 102, the X-ray source 110 and the X-ray obtainer XO may move according to control signals corresponding to the set distances R1 and R2, such that they are spaced by distances optimized for the focal spot size of the X-ray source 110, the properties of the object ob, the FOV of X-ray beams, etc.

Figure 15:
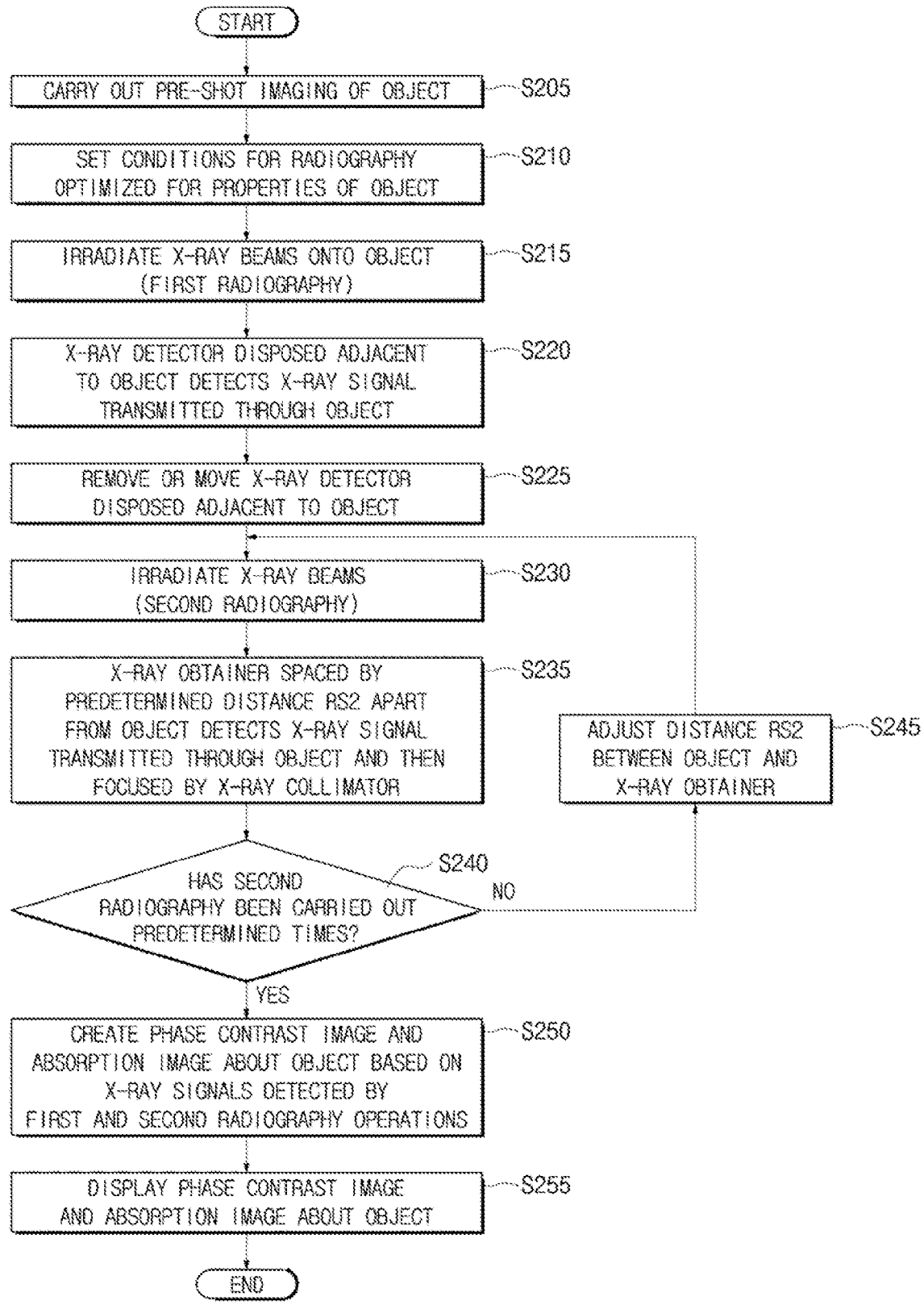
FIG. 15 is a flowchart of a control method of an X-ray imaging apparatus.

FIG. 15 is a flowchart of a control method of an X-ray imaging apparatus.

The exemplary embodiment of FIG. 15 relates to a process of acquiring phase contrast information at two or more locations while adjusting a distance R2 between an object ob and an X-ray obtainer XO, and creating a phase contrast image and an absorption image of the object ob based on the phase contrast information.

Referring to FIGS. 6, 9, and 15, first, pre-shot imaging is carried out on an object ob to acquire a pre-shot image (S205). The pre-shot imaging is carried out prior to radiography in order to set conditions for radiography according to the properties of an object ob, and the pre-shot imaging may be carried out with a low dose of X-rays by adjusting tube current and an X-ray exposure time.

Then, the pre-shot image is analyzed to set conditions for radiography which are optimized according to the properties of the object ob (S210). The conditions that are set may include conditions regarding the generation and irradiation of X-ray beams, and conditions regarding a distance R1 between the X-ray source 110 and the object ob, and a distance R2 between the object ob and the X-ray obtainer XO (see FIG. 6 or 8). More specifically, as a condition regarding the generation of X-ray beams, at least one among a tube voltage, a tube current, target materials of both electrodes, an exposure time, a distance between an anode and a cathode, and a filter type may be set to be optimized for the properties of the object ob. As a condition regarding irradiation of X-rays, the size of an X-ray passing region R of a collimator may be set to be optimized for the properties of the object ob so that a focal spot size can be adjusted so as to be optimized for the properties of the object ob. In addition, conditions regarding the distances R1 and R2 between the X-ray source 110 and the object ob and between the object ob and the X-ray obtainer XO are also set to be optimized for the properties of the object ob by analyzing the pre-shot image.

Thereafter, X-ray beams are irradiated onto the object ob according to the conditions set in step S210 to carry out first radiography (S215). During the first radiography, X-rays are irradiated onto the object ob in order to detect an X-ray signal transmitted through the object ob using the first X-ray detector 120A (see FIG. 6) which is positioned adjacent to the object ob.

Then, an X-ray signal transmitted through the object ob is detected by the X-ray detector 120A positioned adjacent to the object ob (S220).

After the X-ray signal is detected by performing the first radiography, the X-ray detector 120A positioned adjacent to the object ob is removed or moved (S225). At step S225, X-ray beams are transmitted through the object ob so that when second radiography is performed, X-ray beams are incident on the X-ray obtainer XO which is spaced by the predetermined distance R2 apart from the object ob without passing through the X-ray detector 120A.

Thereafter, X-ray beams are irradiated on the object ob according to the conditions set in step S210 in order to perform the second radiography (S230). The second radiography is the operation of irradiating X-rays onto the object ob in order to detect an X-ray signal transmitted through the object ob and which is then focused using the X-ray obtainer XO which is spaced by the predetermined distance R2 apart from the object ob.

An X-ray signal transmitted through the object ob and focused by the X-ray collimator 130 is detected by the X-ray obtainer XO which is spaced by the predetermined distance R2 apart from the object ob (S235).

Thereafter, the image processor 140 determines whether the second radiography has been carried out a predetermined number of times (S240).

In order to create a phase contrast image of the object ob, X-ray signals must be acquired at least two times. Accordingly, when an X-ray signal transmitted through the object ob, which is acquired upon first radiography, and an X-ray signal transmitted through the object ob and focused by the X-ray collimator 130, which is acquired upon second radiography, are given, a phase contrast image of the object ob can be acquired. Also, the second radiography must be carried out one or more times. Upon performing the second radiography, by adjusting the distance R2 between the object ob and the X-ray obtainer XO several times to create a phase contrast image of the object ob based on X-ray signals acquired at a plurality of locations, the performance (e.g., contrast) of the created image may be improved. As the second radiography is carried out more times, a clearer phase contrast image of the object ob can be acquired.

If it is determined that the second radiography has not been carried out the predetermined times ("No" in step S240), the image processor 140 determines that the second radiography process has not yet been completed, and sends a control signal to the exposure controller 160 (see FIG. 9) for the exposure controller 160 to again adjust the distance R2 between the object ob and the X-ray obtainer XO (S245). Then, the process returns to step S230 so that X-ray beams are again irradiated onto the object ob to carry out the second radiography.

If it is determined that the second radiography has been carried out the predetermined times ("Yes" in step S240), the image processor 140 determines that the second radiography of the object ob has been completed, and creates a phase contrast image and an absorption image of the object ob based on the X-ray signals detected by the first and second radiography operations (S250).

Thereafter, the image processor 140 sends a control signal to the display 152 for the display 152 to display the phase contrast image and the absorption image of the object ob (S255).

Figure 16:
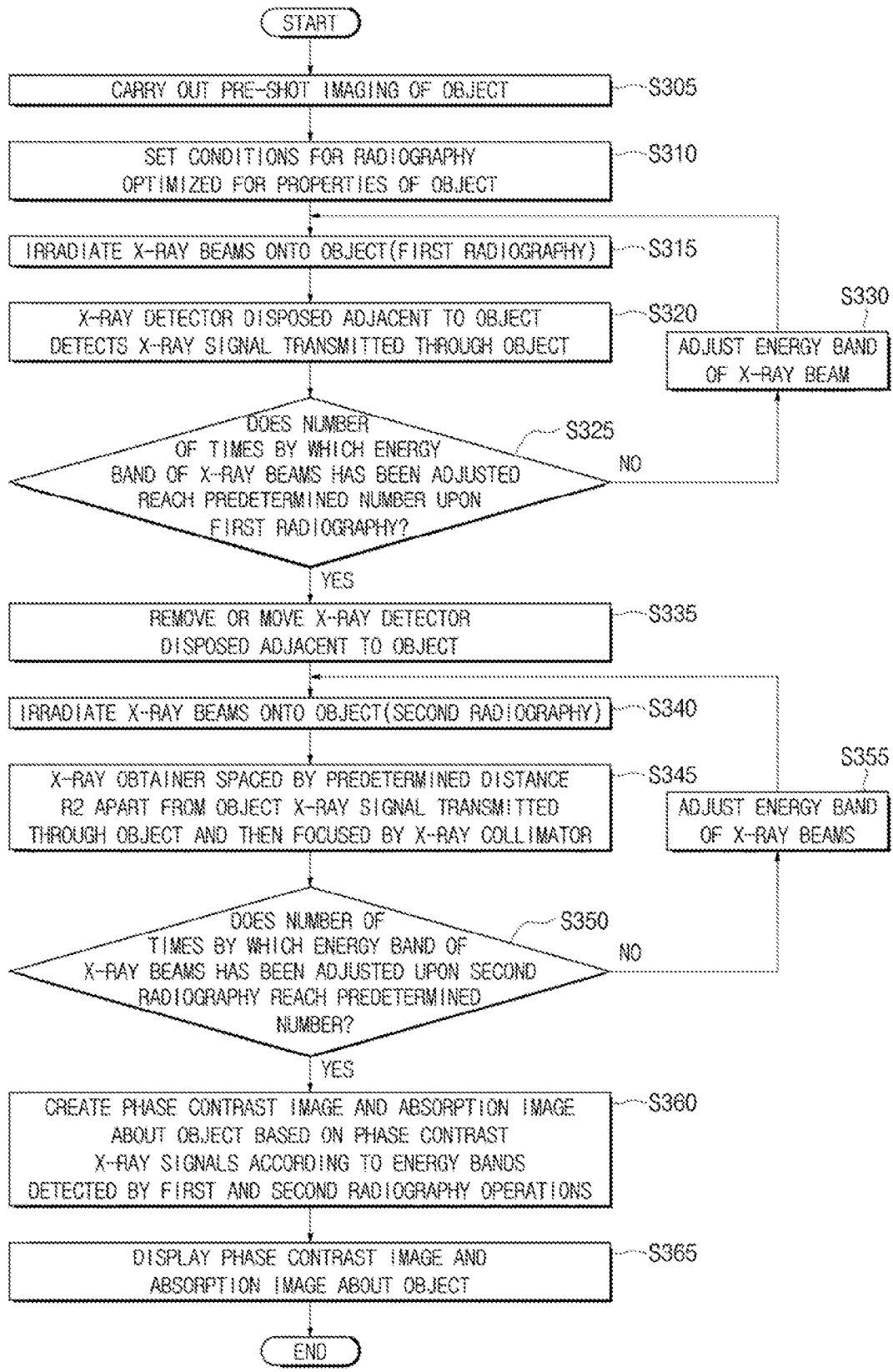
FIG. 16 is a flowchart of a control method of an X-ray imaging apparatus.
Figure 17A:
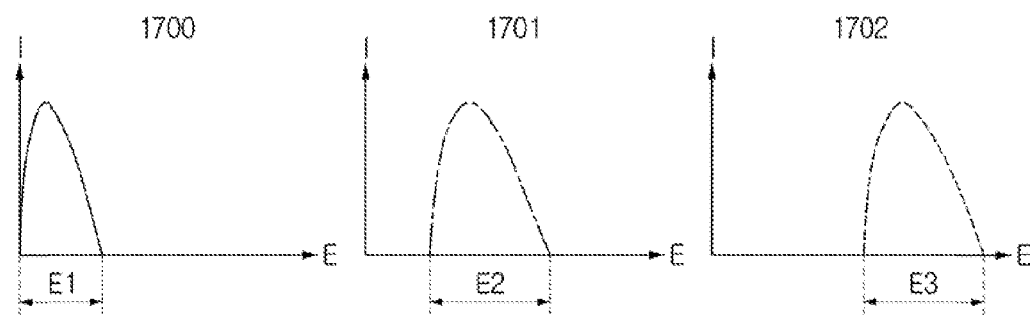
FIG. 17A illustrates graphs showing a plurality of X-ray signals having different energy bands, irradiated from an X-ray source.
Figure 17B:
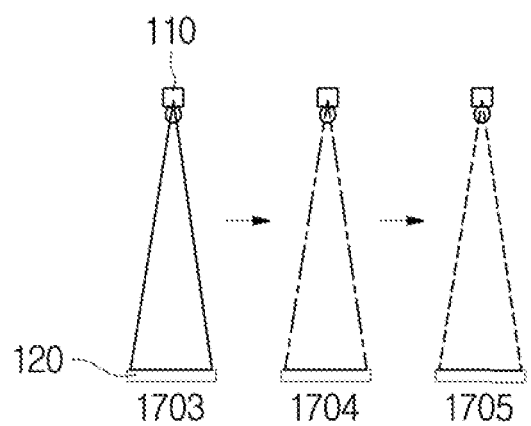
FIG. 17B is a view for describing a process of sequentially detecting the plurality of X-ray signals irradiated from the X-ray source.
Figure 17C:
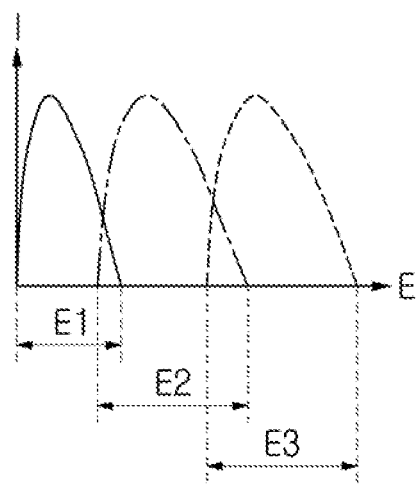
FIG. 17C is a graph showing phase contrast X-ray signals for the individual energy bands, detected by an X-ray detector.

FIG. 16 is a flowchart of a control method of an X-ray imaging apparatus, FIG. 17A is a graph showing a plurality of X-ray signals having different energy bands irradiated from an X-ray source, FIG. 17B is a view for describing a process of sequentially detecting the plurality of X-ray signals irradiated from the X-ray source, and FIG. 17C is a graph showing phase-contrast X-ray signals according to the different energy bands detected by an X-ray detector.

The exemplary embodiment illustrated in FIGS. 16 and 17A to 17C relate to a process of irradiating a plurality of X-ray signals having different energy bands onto an object ob when the distance R2 between the object ob and the X-ray obtainer XO (see FIG. 6) is fixed. Further, the exemplary embodiment illustrates creating a phase contrast image and an absorption image of the object ob based on a plurality of phase contrast X-ray signals acquired through the X-ray detector 120A (see FIG. 6) positioned adjacent to the object ob and the X-ray obtainer XO.

Referring to FIGS. 6, 9, and 16, first, pre-shot imaging is performed on the object ob to acquire a pre-shot image (S305). The pre-shot imaging is carried out prior to performing radiography in order to set conditions for performing the radiography according to the properties of the object ob. The pre-shot imaging may be carried out with a low dose of X-rays by adjusting tube current and an X-ray exposure time.

Then, the pre-shot image is analyzed in order to set conditions for performing radiography which are optimized for the properties of the object ob (S310).

Thereafter, X-ray beams are irradiated onto the object ob according to the conditions set in step S310 and a predetermined energy band to carry out first radiography (S315). In the first radiography X-ray beams are irradiated onto the object ob in order to detect an X-ray signal transmitted through the object ob using the first X-ray detector 120A positioned adjacent to the object ob. In the current exemplary embodiment, X-ray beams having three different energy bands, as illustrated in FIG. 17A, are irradiated onto the object ob when performing the first radiography, and first X-ray beams having an energy band E1 as shown in graph 1700 are irradiated onto the object ob.

Then, an X-ray signal transmitted through the object ob is detected by the X-ray detector 120A located adjacent to the object ob (S320). That is, the X-ray detector 120A detects a signal of the X-ray beams having the energy band E1 irradiated from the X-ray source 110 (see FIG. 6) and then transmitted through the objet ob.

Thereafter, the image processor 140 determines whether the number of times the energy band of the X-ray beams has been adjusted reaches a predetermined number of times during the first radiography (S325). Since the current exemplary embodiment relates to a case in which three types of X-ray beams having energy bands E1, E2, and E3 are irradiated, the predetermined number is set to 3.

If it is determined that the number of times the energy band of the X-ray beams has been adjusted does not reach the predetermined number ("No" in step S325), the image processor 140 determines that the first radiography has been not yet completed, and sends a control signal to the exposure controller 160 (see FIG. 9) for the exposure controller 160 to adjust the energy band of the X-ray beams that are irradiated by the X-ray source 110 (S330). Then, the process returns to step S315 so that X-ray beams having an adjusted energy band are irradiated onto the object ob to carry out first radiography. Referring to FIG. 17A, X-ray beams having an energy band E1 are first irradiated onto the object ob, and then the energy band of the X-ray beams are sequentially adjusted from the energy band E1 (as shown in graph 1700) to an energy band E2 (as shown in graph 1701) and then from the energy band E2 to an energy band E3 (as shown in graph 1702).

If it is determined that the number of times the energy band of the X-ray beams has been adjusted reaches the predetermined number ("Yes" in step S325), the image processor 140 determines that all X-ray signals have been detected through the first radiography. Then, as illustrated in FIG. 17C, phase contrast X-ray signals according to the individual energy bands can be sequentially acquired.

After all of the X-ray signals are detected through the first radiography, the X-ray detector 120A located adjacent to the object ob is removed or moved (S335). At step S235, X-ray beams transmitted through the object ob upon second radiography are aimed to be incident on the X-ray obtainer XO which is spaced by the predetermined distance R2 apart from the object ob without passing through the X-ray detector 120A.

Thereafter, X-ray beams are irradiated on the object ob according to the conditions set in step S310 to carry out second radiography (S340). The second radiography is the operation of irradiating X-ray beams onto the object ob in order to detect an X-ray signal transmitted through the object ob and then focused using the X-ray obtainer XO which is spaced by the predetermined distance R2 apart from the object ob. In the current exemplary embodiment, X-ray beams having three different energy bands, as illustrated in FIG. 17A, are irradiated onto the object ob upon the second radiography, and X-ray beams having an energy band E1 (graph 1700 of FIG. 17A) are first irradiated onto the object ob.

Then, an X-ray signal transmitted through the object ob and then focused by the X-ray collimator 130 is detected by the X-ray obtainer XO (S345). That is, as illustrated at 1703 of FIG. 17B, the X-ray detector 120A located adjacent to the object ob detects a signal of the X-ray beams having the energy band E1 irradiated from the X-ray source 110 (see FIG. 6) and then transmitted through the objet ob.

Thereafter, the image processor 140 determines whether the number of times by which the energy band of the X-ray beams has been adjusted at the second radiography reaches a predetermined number (S350). Since the current exemplary embodiment relates to a case in which three types of X-ray beams having three energy bands E1, E2, and E3 are irradiated, the predetermined number is set to three.

If it is determined that the number of times by which the energy band of the X-ray beams has been adjusted by the second radiography does not reach a predetermined number ("No" in step S350), the image processor 140 determines that the second radiography has not yet been completed, and sends a control signal to the exposure controller 160 for the exposure controller 160 to adjust the energy band of the X-ray beams that are irradiated by the X-ray source 110 (S355). Then, the process returns to step S340 so that X-ray beams having an adjusted energy band are irradiated onto the object ob to carry out the second radiography. Referring to FIG. 17A, X-ray beams having an energy band E1 are first irradiated onto the object ob, and then the energy band of the X-ray beams is sequentially adjusted from the energy band E1 to an energy band E2 and then from the energy band E2 to an energy band E3.

Meanwhile, upon determining that the number of times by which the energy band of the X-ray beams has been adjusted reaches the predetermined number ("Yes" in step S350), the image processor 140 determines that all of the X-ray signals have been detected through the second radiography. Then, as illustrated in FIG. 17C, phase contrast X-ray signals according to the individual energy bands can be sequentially acquired. The image processor 140 creates a phase contrast image and an absorption image of the object ob based on the X-ray signals according to the energy bands detected by the first and second radiography operations (S360).

Then, the image processor 140 sends a control signal to the display 152s for the display 152 to display the phase contrast image and the absorption image about the object ob (S365).

According to the exemplary embodiment as described above, the X-ray source 110 irradiates X-ray beams having different energy bands sequentially, and the X-ray detector 120 detects the X-ray beams sequentially, thereby acquiring phase contrast image signals having different characteristics. Accordingly, although the irradiation of X-ray beams should be done several times, deterioration of picture quality due to motion artifacts can be prevented since the X-ray obtainer XO does not need to move.

Figure 18:
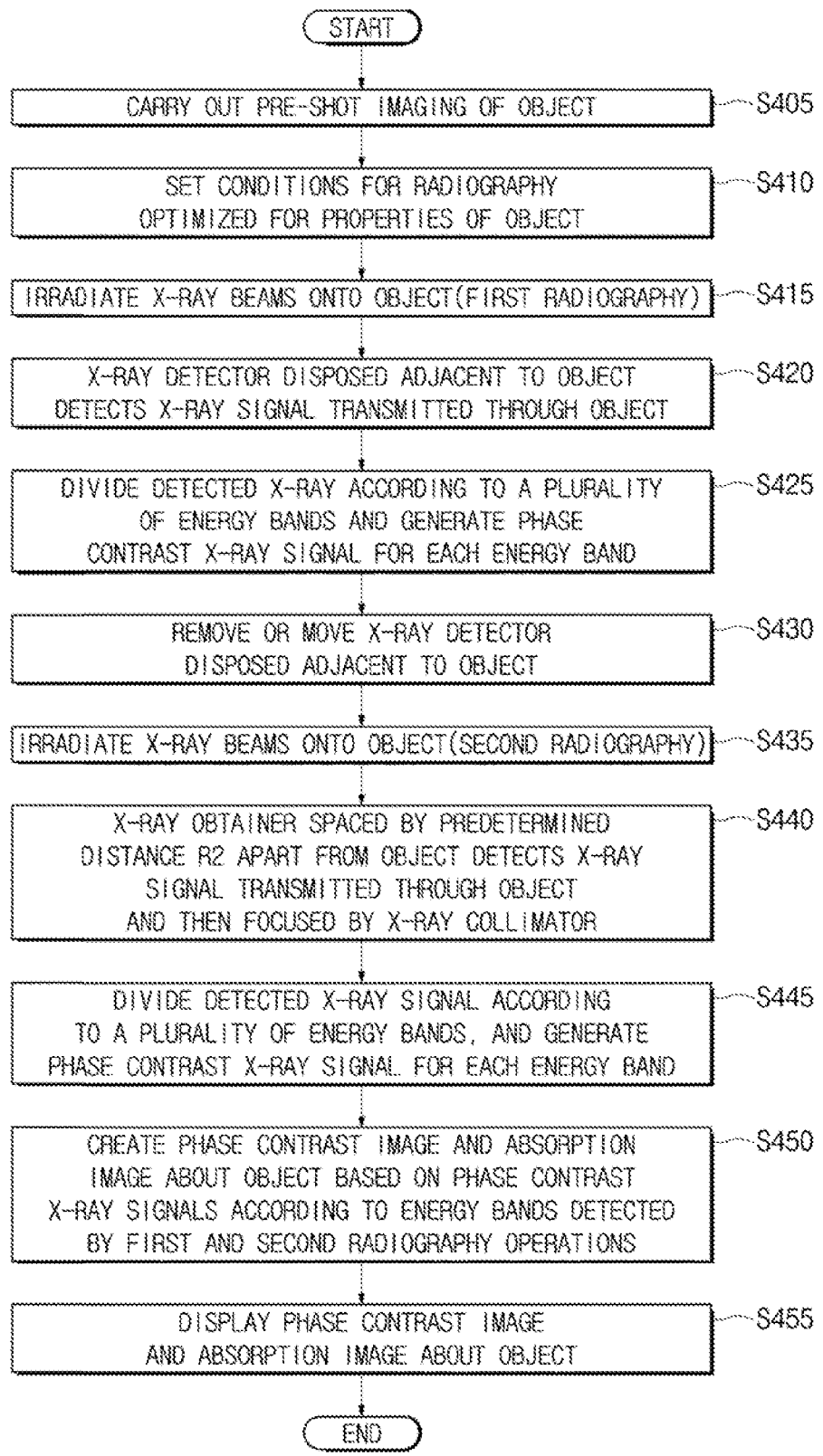
FIG. 18 is a flowchart of a control method of an X-ray imaging apparatus.
Figure 19A:
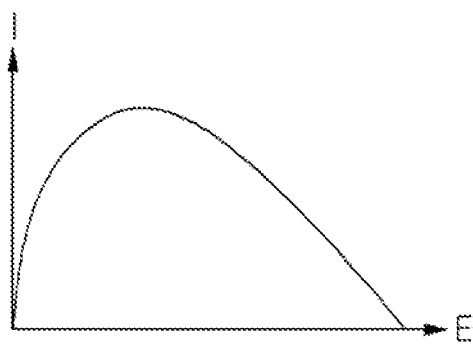
FIG. 19A is a graph showing a wide band of an X-ray signal irradiated from an X-ray source.
Figure 19B:
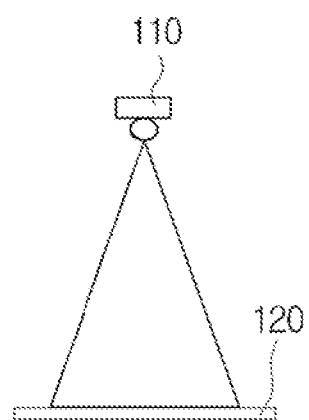
FIG. 19B is a view for describing a process of detecting the wide band of the X-ray signal irradiated from the X-ray source.
Figure 19C:
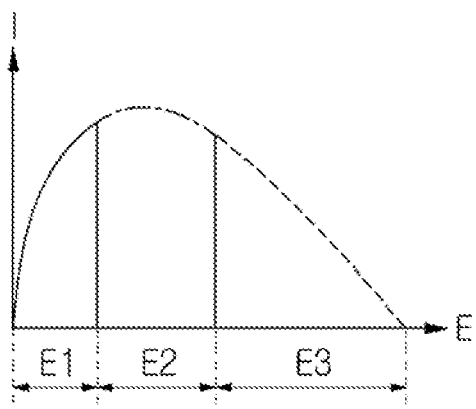
FIG. 19C is a graph showing phase contrast X-ray signals for the individual energy bands, detected by energy-dividable X-ray detectors.

FIG. 18 is a flowchart of a control method of an X-ray imaging apparatus, FIG. 19A is a graph showing a wide band of an X-ray signal irradiated from an X-ray source, FIG. 19B is a view for describing a process of detecting the wide band of the X-ray signal irradiated from the X-ray source, and FIG. 19C is a graph showing phase contrast X-ray signals according to different energy bands, detected by energy-dividable X-ray detectors.

The exemplary embodiment illustrated in FIGS. 18 and 19A to 19C relate to a process of irradiating a wide band of an X-ray signal onto an object ob when the distance R2 between the object ob and the X-ray obtainer XO (see FIG. 6) is fixed, and creating a phase contrast image and an absorption image of the object ob based on a plurality of phase contrast X-ray signals acquired by the energy-dividable X-ray detectors 120A and 120B (see FIG. 6). The first X-ray detector 120A and the second X-ray detector 120B can be energy-dividable X-ray detectors as discussed in the current embodiment.

Referring to FIGS. 6, 9, and 18, first, pre-shot imaging is carried out on an object ob to acquire a pre-shot image of the object ob (S405). The pre-shot imaging is carried out prior to radiography in order to set conditions for radiography according to the properties of an object ob. The pre-shot imaging may be carried out with a low dose of X-rays by adjusting tube current and an X-ray exposure time.

Then, the pre-shot image is analyzed to set conditions for performing radiography which is optimized for the properties of the object ob (S410).

Thereafter, X-ray beams are irradiated onto the object ob according to the conditions set in step S410 and a predetermined energy band (a wide energy band) to carry out first radiography (S415). The first radiography is an operation of irradiating X-ray beams onto the object ob in order to detect an X-ray signal transmitted through the object ob using the first X-ray detector 120A located adjacent to the object ob. In the current exemplary embodiment, during the first radiography, as illustrated in FIG. 19A, X-ray beams having a wide energy band are irradiated onto the object ob.

Then, an X-ray signal transmitted through the object ob is detected by the X-ray detector 120A located adjacent to the object ob (S420). That is, as illustrated in FIG. 19B, the X-ray detector 120A detects a signal of the X-ray beams having the wide energy band, irradiated from the X-ray source 110 (see FIG. 6) and then transmitted through the object ob.

Then, the X-ray detector 120A divides the detected X-ray signal according to a plurality of energy bands to create a phase contrast X-ray signal for each energy band (S425). The X-ray detector 120 may be embodied as a photon counting detector (PCD) to count the number of photons having a higher energy than threshold energy among photons included in the detected X-ray signal. The ranges of energy bands that are to be divided and the number of energy bands that are to be divided may be set based on a desired image definition or resolution, or according to the properties of the object ob. The energy-dividable X-ray detector 120A located adjacent to the object ob may divide, as illustrated in FIG. 19C, the X-ray signal transmitted through the object ob according to three energy bands E1, E2, and E3.

After all of the X-ray signals are detected through the first radiography, the X-ray detector 120A located adjacent to the object ob is removed or moved (S430). At step S430, X-ray beams transmitted through the object ob during the second radiography are aimed to be incident on the X-ray obtainer XO which is spaced by the predetermined distance R2 apart from the object ob without passing through the X-ray detector 120A.

Thereafter, X-ray beams are irradiated onto the object ob according to the conditions set in step 410 and a predetermined energy band (a single wide energy band) to carry out second radiography (S435). The second radiography is the operation of irradiating X-ray beams onto the object ob in order to detect an X-ray signal transmitted through the object ob and then focused using the X-ray obtainer XO which is spaced by the predetermined distance R2 apart from the object ob. In the current exemplary embodiment, during the second radiography, as illustrated in FIG. 19A, X-ray beams having a wide energy band are irradiated onto the object ob.

Then, an X-ray signal transmitted through the object ob and then focused by the X-ray collimator 130 is detected using the X-ray obtainer XO which is spaced by the predetermined distance R2 apart from the object ob (see FIG. 6) (S440). That is, as illustrated in FIG. 19B, the X-ray detector 120B included in the X-ray obtainer XO which is spaced by the predetermined distance R2 apart from the object ob detects a signal of the X-ray beams having the wide energy band irradiated from the X-ray source 110 and then transmitted through the object ob.

Thereafter, the X-ray detector 120B divides the detected X-ray signal according to a plurality of energy bands to create a phase contrast X-ray signal for each energy band (S445). To do this, the X-ray detector 120B may be a photon counting detector (PCD) to count the number of photons having a higher energy than threshold energy among photons included in the detected X-ray signal. The ranges of energy bands that are to be divided, and the number of energy bands that are to be divided may be set based on a desired image definition or resolution, or according to the properties of the object ob. The energy-dividable X-ray detector 120B located adjacent to the object ob may divide, as illustrated in FIG. 19C, the X-ray signal transmitted through the object ob according to three energy bands E1, E2, and E3.

After all X-ray signals are detected through the second radiography, the image processor 140 creates a phase contrast image and an absorption image of the object ob based on the phase contrast X-ray signals according to the energy bands created by the first and second radiography operations (S450).

Thereafter, the image processor 140 sends a control signal to the display 152 for the display 152 to display the phase contrast image and the absorption image of the object ob (S455).

According to the exemplary embodiment as described above, the X-ray source 110 irradiates a wide band of X-ray beams a single time, and the X-ray detectors 120 detect and divide the wide band of X-ray beams, thereby acquiring phase contrast image signals having different characteristics according to the energy bands. According to the current exemplary embodiment, since it is unnecessary to irradiate X-ray beams several times onto an object, the object will be exposed to a smaller dose of X-rays, and since the X-ray obtainer XO does not need to move, deterioration of picture quality due to motion artifacts can be prevented.

Although a few exemplary embodiments have been shown and described, it would be appreciated by those skilled in the art that changes may be made in these exemplary embodiments without departing from the principles and spirit of the inventive concept, the scope of which is defined in the claims and their equivalents.

What is claimed is:

1. An X-ray imaging apparatus comprising:
   an X-ray source configured to generate X-ray beams and configured to emit the X-ray beams in an emission direction onto an object;
   a first X-ray detector located adjacent to the object and configured to detect X-ray beams transmitted through the object and configured to generate a first phase contrast signal based on the detected X-ray beams;
   an X-ray obtainer including an X-ray collimator and a second X-ray detector,
   wherein the X-ray collimator is spaced apart from the object by a predetermined distance, and configured to focus the X-ray beams transmitted through the object, and
   wherein the second X-ray detector is configured to detect the focused X-ray beams and to generate a second phase contrast signal based on the detected X-ray beams; and
   an image processor configured to create a phase contrast image and an absorption image of the object based on the first phase contrast signal generated by the first X-ray detector and the second phase contrast signal generated by the second X-ray detector,
   wherein the X-ray source and the X-ray collimator are configured to move in a direction parallel to the emission direction.

2. The X-ray imaging apparatus according to claim 1, wherein the X-ray collimator uses polycapillary optics.

3. The X-ray imaging apparatus according to claim 1, wherein the second X-ray detector is configured to detect the X-ray beams focused by the X-ray collimator and is configured to generate a phase contrast signal based on the detected X-ray beams.

4. The X-ray imaging apparatus according to claim 1, wherein the second X-ray detector detects the X-ray beams focused by the X-ray collimator after the first X-ray detector is removed or bent at a predetermined angle.

5. The X-ray imaging apparatus according to claim 1, wherein the X-ray source is configured to generate spatial coherent X-ray beams.

6. The X-ray imaging apparatus according to claim 1, wherein each of the first X-ray detector and the second X-ray detector is a Photon Counting Detector (PCD) configured to count a number of photons having a higher energy value than a threshold energy value corresponding to each of a plurality of energy bands among photons included in the detected X-ray beams; and
   wherein each of the first X-ray detector and the second X-ray detector divides the detected X-ray beams according to the plurality of energy bands, and generates a phase contrast image signal for each of the plurality of energy bands.

7. The X-ray imaging apparatus according to claim 1, further comprising an exposure controller configured to set one or more conditions that are applied during radiography by analyzing a pre-shot image of the object.

8. The X-ray imaging apparatus according to claim 7, wherein the exposure controller is configured to analyze the pre-shot image to determine properties of the object, and configured to adjust a focal spot size of the X-ray source based on the properties of the object.

9. The X-ray imaging apparatus according to claim 8, wherein the exposure controller adjusts at least one of a distance between the X-ray source and the object, and a distance between the object and the X-ray obtainer, based on at least one of the properties of the object, the focal spot size of the X-ray source, and a Field Of View (FOV) of the X-ray source.

10. The X-ray imaging apparatus according to claim 1, further comprising a display configured to display the phase contrast image and the absorption image of the object.

11. A control method of an X-ray image apparatus, the method comprising:
generating first X-ray beams at an X-ray source, and emitting the first X-ray beams in an emission direction onto an object;
detecting by a first X-ray detector located adjacent to the object, the first X-ray beams transmitted through the object, dividing the detected first X-ray beams according to a first plurality of energy bands, and generating a first phase contrast image signal for each of the first plurality of energy bands;
generating second X-ray beams at the X-ray source, and emitting the second X-ray beams onto the object;
focusing the second X-ray beams transmitted through the object at an X-ray collimator which is spaced apart from the object by a predetermined distance;
detecting by a second X-ray detector coupled with the X-ray collimator the focused second X-ray beams, dividing the detected second X-ray beams according to a second plurality of energy bands, and generating a second phase contrast image signal for each of the second plurality of energy bands; and
creating a phase contrast image and an absorption image of the object based on the first phase contrast image signal generated for each of the first plurality of energy bands and the second phase contrast image signal generated for each of the second plurality of energy bands,
wherein the focusing the second X-ray beams comprises moving the X-ray source and the X-ray collimator in a direction parallel to the emission direction.

12. The control method according to claim 11, wherein the first X-ray beams and the second X-ray beams are spatial coherent X-ray beams.

13. The control method according to claim 11, wherein the generating the second phase contrast image signal for each of the second plurality of energy bands is performed after the first X-ray detector located adjacent to the object is removed or bent at a predetermined angle.

14. The control method according to claim 11, wherein the generating the first phase contrast image signal for each of the first plurality of energy bands and the generating the second phase contrast image signal for each of the second plurality of energy bands comprises counting a number of photons having a higher energy value than a threshold energy value corresponding to each of the first plurality of energy bands and the second plurality of energy bands among photons included in the detected first X-ray beams and the second X-ray beams, respectively.

15. The control method according to claim 11, further comprising:
carrying out pre-shot imaging of the object to acquire a pre-shot image of the object; and
analyzing the pre-shot image of the object to set one or more conditions that are applied during radiography.

16. The control method according to claim 11, further comprising displaying the phase contrast image and the absorption image of the object.

17. A control method of an X-ray imaging apparatus, the method comprising:
generating first X-ray beams at an X-ray source, and emitting the first X-ray beams in an emission direction onto an object;
at a first X-ray detector located adjacent to the object, detecting the first X-ray beams transmitted through the object, and generating a first phase contrast signal based on the detected first X-ray beams;
generating second X-ray beams at the X-ray source, and irradiating the second X-ray beams onto the object;
at an X-ray collimator which is spaced apart from the object by a predetermined distance, focusing the second X-ray beams transmitted through the object;
at a second X-ray detector coupled with the X-ray collimator, detecting the focused second X-ray beams, and generating a second phase contrast signal based on the detected second X-ray beams; and
creating a phase contrast image and an absorption image of the object based on the first phase contrast signal and the second phase contrast signal,
wherein the focusing the second X-ray beams comprises moving the X-ray source and the X-ray collimator in a direction parallel to the emission direction.

18. The control method according to claim 17, wherein the first X-ray beams and the second X-ray beams are spatial coherent X-ray beams.

19. The control method according to claim 17, wherein the generating the second phase contrast image signal for each of the second plurality of energy bands is performed after the first X-ray detector located adjacent to the object is removed or bent at a predetermined angle.

20. The control method according to claim 17, further comprising displaying the phase contrast image and the absorption image of the object.

21. An X-ray imaging apparatus comprising:
an X-ray source configured to generate X-ray beams and configured to emit the X-ray beams in an emission direction onto an object;
a first X-ray detector located adjacent to the object and configured to detect X-ray beams transmitted through the object and configured to generate a first phase contrast signal based on the detected X-ray beams;
a second X-ray detector located after the first X-ray detector and configured to detect X-ray beams transmitted through the object and focused by an X-ray collimator when the first X-ray detector is moved and configured to generate a second phase contrast signal based on the detected X-ray beams, and
an image processor configured to create a phase contrast image and an absorption image of the object based on the first phase contrast signal generated by the first X-ray detector and the second phase contrast signal generated by the second X-ray detector, wherein the X-ray source and the X-ray collimator are configured to move in a direction parallel to the emission direction.

22. The X-ray imaging apparatus according to claim 21, wherein the X-ray collimator is located between the first X-ray detector and the second X-ray detector.

23. The X-ray imaging apparatus according to claim 21, wherein the first X-ray detector is moved so that the second X-ray detector detects the X-ray beams transmitted by the X-ray source through the object.

* * * * *